(12) United States Patent
Huscroft et al.

(10) Patent No.: US 6,479,486 B2
(45) Date of Patent: Nov. 12, 2002

(54) AZABICYCLIC SPIROETHER DERIVATIVES AND THEIR USE AS THERAPEUTIC AGENTS

(75) Inventors: Ian Thomas Huscroft, Bishops Stortford (GB); Janusz Jozef Kulagowski, Sawbridgeworth (GB); Piotr Antoni Raubo, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 10/115,629

(22) Filed: Apr. 1, 2002

(65) Prior Publication Data

US 2002/0147207 A1 Oct. 10, 2002

(30) Foreign Application Priority Data

Apr. 10, 2001 (GB) ............................................. 0108973

(51) Int. Cl.[7] .................. A61K 31/438; C07D 491/107
(52) U.S. Cl. .................... 514/233.5; 514/278; 544/127; 546/18
(58) Field of Search ............................ 514/233.5, 278; 544/127; 546/18

(56) References Cited

U.S. PATENT DOCUMENTS 6,071,927 A * 6/2000 Baker et al. ................. 514/278

* cited by examiner

Primary Examiner—Fiona T. Powers
(74) Attorney, Agent, or Firm—J. Eric Theis; Melvin Winokur

(57) ABSTRACT

The present invention relates compounds of the formula (I):

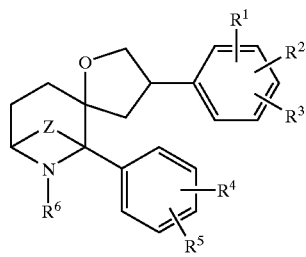

wherein

Z is —$CR^9R^{10}CH_2$— or —$CH_2CR^9R^{10}$—;

and $R^1$, $R^2$, $R^3$, $R^4$, $R^5$ and $R^6$ are as defined herein. The compounds are of particular use in the treatment or prevention of depression, anxiety, pain, inflammation, migaine, emesis or postherpetic neuralgia.

16 Claims, No Drawings

AZABICYCLIC SPIROETHER DERIVATIVES AND THEIR USE AS THERAPEUTIC AGENTS

CROSS REFERENCE TO RELATED APPLICATIONS

This application claims priority under 35 U.S.C. §119 from GB Application No. 0108973.9, filed Apr. 10, 2001.

This invention relates to a class of azabicyclic compounds which are useful as tachykinin antagonists. More particularly, the compounds of the invention are spiroether derivatives of 1-phenyl-8-azabicyclo[3.2.1]octane, which are useful as neurokinin 1 (NK-1) receptor antagonists.

The present invention provides compounds of the formula (I):

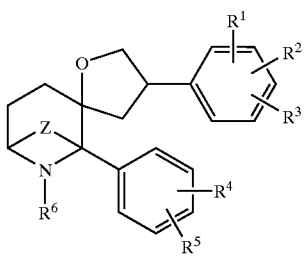

wherein

Z is —$CR^9R^{10}CH_2$— or —$CH_2CR^9R^{10}$—;

$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$, $OSO_2R^a$, $NR^aCOR^{12}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen, sulphur, NH or $NR^c$, which ring is optionally substituted by one, two or three groups selected from hydroxy, $C_{1-4}$alkyl, $C_{1-3}$alkoxy$C_{1-3}$alkyl, fluoro$C_{1-4}$alkyl, phenyl, =O or =S, where $R^c$ is $C_{1-4}$alkyl, hydroxy$C_{1-4}$alkyl, $C_{1-4}$alkoxy$C_{1-4}$alkyl, fluoro$C_{1-4}$alkyl, phenyl or benzyl;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{12}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, CONHphenyl($C_{1-4}$alkyl), $COCO_2R^a$, $CONHNR^aR^b$, $C(S)NR^aR^b$, $CONR^aC_{1-6}$alkylR$^{14}$, $CONR^{11}C_{2-6}$alkenyl, $CONR^{11}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —Y—$NR^7R^8$ where Y is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ represents hydrogen or $C_{1-4}$alkyl, $C_{1-4}$alkoxy, $C_{3-7}$cycloalkyl, $C_{3-7}$cycloalkyl$C_{1-4}$alkyl, or $C_{2-4}$alkyl substituted by a group selected from $C_{1-4}$alkoxy, hydroxyl, $CO_2R^a$, $NR^aR^b$, aryl, aryloxy, heteroaryl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy, phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is as previously defined;

or $R^7$, $R^8$ and the nitrogen atom to which they are attached form a non-aromatic azabicyclic ring system of 6 to 12 ring atoms;

or Y, $R^7$ and the nitrogen atom to which they are attached form a heteroaliphatic ring to 4 to 7 ring atoms which may optionally contain an oxygen ring atom;

$R^9$ represents hydrogen, hydroxy, oxo, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, aryl, aryl(CH$_2$), aryloxy, aryl(CH$_2$)oxy, cyano, halogen, $NR^7R^8$, $CH_2NR^7R^8$, $SR^{12}$, $SOR^{12}$, $SO_2R^{12}$, $OSO_2R^{12}$, $NR^aCOR^{12}$, CH(OH)$R^{12}$, $COR^{12}$, $CO_2R^{12}$, $CONR^7R^8$, $CH_2OR^{13}$, heteroaryl or heteroaryl$C_{1-4}$alkyl, wherein $R^a$ is as previously defined;

$R^{10}$ represents hydrogen, halogen or hydroxy;

$R^{11}$ represents hydrogen or $C_{1-6}$alkyl;

$R^{12}$ represents hydrogen, $C_{1-6}$alkyl, $C_{1-6}$alkoxy, fluoro$C_{1-6}$alkyl or phenyl optionally substituted by one, two or three substituents selected from $C_{1-6}$alkyl, $C_{1-6}$alkoxy, halogen or trifluoromethyl;

$R^{13}$ represents $C_{1-4}$alkyl substituted by a group selected from hydroxy, $COR^a$, $CO_2R^a$, $CONR^aR^b$ and heteroaryl, where $R^a$ is as previously defined;

$R^{14}$ represents $OR^a$, $CONR^aR^b$ or heteroaryl;

and pharmaceutically acceptable salts or N-oxides thereof.

A preferred class of compound of formula (I) is that wherein $R^1$ is a $C_{1-6}$alkoxy, fluoro$C_{1-6}$alkoxy or $C_{3-7}$cycloalkoxy group, or $R^1$ together with the group $R^2$ forms a 5-membered saturated ring containing one oxygen atom, which ring is optionally substituted by a methyl group.

A particularly preferred class of compound of formula (I) is that wherein $R^1$ is methoxy, trifluoromethoxy, 2,2,2-trifluoroethoxy, 2,2-difluoroethoxy, 2-fluoroethoxy, cyclopropoxy or $R^1$ together with the group $R^2$ represents —OCH($CH_3$)$CH_2$— or —N($CH_3$)C(O)C($CH_3$)$_2$— to complete a 5-membered saturated ring, or —CH(OH)$CH_2$OC($CH_3$)($CF_3$)—, —$CH_2CH_2$C(O)N($CH_3$)— or —CH(OH)$CH_2$C(O)N($CH_3$)— to complete a 6-membered saturated ring. Most especially, $R^1$ is methoxy or cyclopropoxy.

Another preferred class of compound of formula (I) is that wherein $R^2$ is a hydrogen, fluorine or chlorine atom, especially a hydrogen atom.

A further preferred class of compound of formula (I) is that wherein $R^3$ is a hydrogen or halogen atom or a fluoro$C_{1-6}$alkoxy group, especially fluorine, trifluoromethoxy or 2,2,2-trifluoroethoxy, or a 5-membered aromatic heterocyclic group as previously defined. Most preferably, $R^3$ is trifluoromethoxy or 5-(trifluoromethyl)tetrazol-1-yl, and especially trifluoromethoxy.

A particularly preferred class of compound of formula (I) is that wherein $R^1$ is attached at the 2-position of the phenyl ring and $R^3$ is attached at the 5-position of the phenyl ring.

A further preferred class of compound of formula (I) is that wherein $R^4$ is a hydrogen atom or a fluorine atom.

Another preferred class of compound of formula (I) is that in which $R^5$ is a hydrogen atom.

A further preferred class of compound of formula (I) is that wherein $R^6$ is a hydrogen atom or a $C_{1-6}$alkyl group. Most especially, $R^6$ is hydrogen or methyl.

Also preferred is the class of compound of formula (I) in which $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from 1,3-imidazol-4-yl, 1,2,4-triazol-3-yl, 1,2,3-triazol-4-yl, 2-oxo-1,3-imidazol-4-yl, and 3-oxo-1,2,4-triazol-5-yl, any of which rings being optionally substituted by the group —Y—$NR^7R^8$.

Particularly preferred heterocyclic rings are selected from:

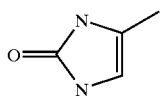 ; 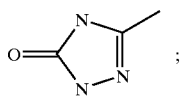 ;

-continued

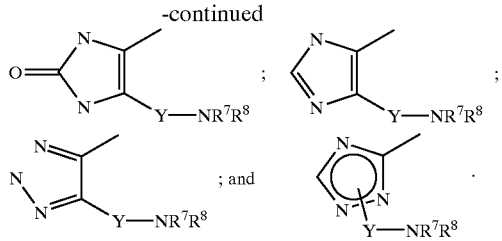

Another preferred class of compound of formula (I) is that wherein $R^9$ represents hydrogen, hydroxy, oxo, $C_{1-6}$alkoxy, $C_{1-6}$alkoxy$C_{1-4}$alkyl, hydroxy$C_{1-4}$alkyl, cyano, $NR^7R^8$, $CH_2NR^7R^8$, $SO_2R^a$, $CH(OH)R^{12}$, $COR^{12}$, $CO_2R^{12}$, $CONR^7R^8$, phenyl, heteroaryl, heteroaryl$C_{1-4}$alkyl or $CH_2OR^{13}$, where said phenyl is optionally substituted by one or two substituents selected from $C_{1-4}$alkyl, $C_{1-4}$alkoxy, halogen or trifluoromethyl.

A further preferred class of compound of formula (I) is that wherein $R^9$ represents hydrogen, $SO_2R^d$ (in particular where $R^d$ is phenyl) or $CONR^7R^8$ (in particular where $R^7$ is $C_{1-4}$alkyl or $C_{2-4}$alkyl substituted by a hydroxyl or $C_{1-2}$alkoxy group and $R^8$ is hydrogen, $C_{1-4}$alkyl, $C_{1-4}$alkoxy or $C_{2-4}$alkyl substituted by a hyxdroxyl or $C_{1-2}$alkoxy group, or $R^7$ and $R^8$, together with the nitrogen atom to which they are attached, form an azetidinyl, pyrrolidinyl, piperidinyl, morpholino, thiomorpholino, piperazino or piperazino group substituted on the nitrogen atom by a $C_{1-4}$alkyl, hydroxy$C_{1-2}$alkyl, $C_{1-4}$alkoxy$C_{1-2}$alkyl, phenyl or benzyl group).

Another preferred class of compound of formula (I) is that wherein $R^{10}$ represents hydrogen, fluorine or hydroxy, and in particular that wherein $R^{10}$ is hydrogen.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

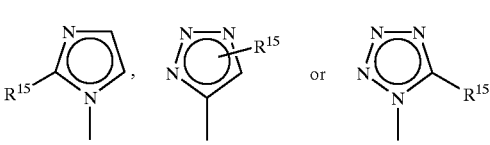

where $R^{15}$ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are hydrogen or $C_{1-4}$alkyl, and r is zero, 1 or 2.

The optionally substituted tetrazolyl group is particularly preferred.

$R^{15}$ is preferably hydrogen, $C_{1-4}$alkyl, especially methyl, $CF_3$, $(CH_2)_rCONR^aR^b$, $SOR^a$ or $SO_2R^a$ where $R^a$, $R^b$ and r are as previously defined. Most especially, $R^{15}$ is $CF_3$.

One favoured group of compounds of the present invention is of the formula (Ia) and pharmaceutically acceptable salts thereof:

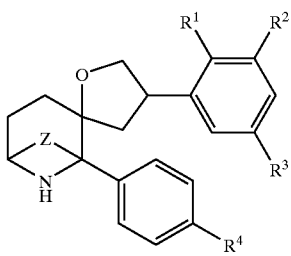

(Ia)

wherein $R^1$, $R^2$, $R^3$ and $R^4$ are as defined in relation to formula (I) and Z is —$CR^9R^{10}CH_2$—.

With respect to compounds of the formula (I), Y (where present), may be a linear, branched or cyclic group. Favourably Y contains 1 to 4 carbon atoms and most favourably 1 or 2 carbon atoms. A particularly favourable group Y is $CH_2$.

With respect to compounds of the formula (I), $R^7$ may aptly be a $C_{1-4}$alkyl group or a $C_{2-6}$alkyl group substituted by a hydroxyl or $C_{1-2}$alkoxy group, $R^8$ may aptly be hydrogen or a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 4, 5 or 6 membered heteroaliphatic ring containing one or two heteroatoms selected from N, O and S, suitable rings include azetidinyl, pyrrolidino, piperidino, piperazino, morpholino, or thiomorpholino. Particularly preferred are nitrogen containing heteroaliphatic rings, especially pyrrolidino and morpholino rings.

Particularly suitable moieties —Y—$NR^7R^8$ include those wherein Y is $CH_2$ or $CH_2CH_2$ and $NR^7R^8$ is amino, methylamino, dimethylamino, diethylamino, azetidinyl, pyrrolidino and morpholino.

In particular, Y is preferably $CH_2$ and $NR^7R^8$ is preferably dimethylamino, azetidinyl or pyrrolidino, especially dimethylamino.

When any variable occurs more than one time in formula (I) or in any substituent, its definition on each occurrence is independent of its definition at every other occurrence.

It will be appreciated that, where $R^9$ represents an oxo (=O) group, then $R^{10}$ will be absent and the group Z will in fact represent —C(O)$CH_2$— or —$CH_2$C(O)—.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" mean a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

As used herein, the term "hydroxy$C_{1-6}$alkyl" means a $C_{1-6}$alkyl group, in which one or more (in particular 1 to 3) hydrogen atoms have been replaced by a hydroxy group. Preferred are hydroxy$C_{1-3}$alkyl groups, especially where one hydrogen atom has been replaced by a hydroxy group, for example, $CH_2OH$, $CH_2CH_2OH$ and $C(CH_3)_2OH$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "aryl" as a group or part of a group means a monocyclic, fused-bicyclic or linear bicyclic aromatic ring containing 6, 10 or 12 carbon atoms, any of which rings is optionally substituted by one, two or three substituents selected from halogen, $C_{1-6}$alkyl, $C_{1-6}$alkoxy, or trifluoromethyl. Particular examples of such groups include phenyl, naphthyl and biphenyl. Phenyl is especially preferred.

As used herein, the term "heteroaryl" as a group or part of a group means a monocyclic or fused-bicyclic heteroaromatic ring containing between 5 and 10 ring members, of which 1 to 4 may be heteroatoms selected from N, O and S, and wherein any of which rings is optionally substituted by one or two substituents selected from halogen, $C_{1-6}$alkyl, $C_{1-6}$alkoxy, trifluoromethyl or phenyl. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole and benzthiazole. Furanyl, thienyl, imidazolyl, oxazolyl, isoxazolyl, thiazolyl, triazolyl, tetrazolyl, and pyridyl are particularly preferred. Where said rings are substituted, preferred substituents include methyl and phenyl groups.

When used herein the term "halogen" means fluorine, chlorine, bromine and iodine. The most apt halogens are fluorine and chlorine of which fluorine is preferred, unless otherwise stated.

Specific compounds within the scope of this invention include:
  (1R*,2R*,4'S*,5S*)-2',3',4',5'-tetrahydro-4'-(2-methoxy-5-trifluoromethoxyphenyl)-1-phenylspiro[8-azabicyclo[3.2.1]octane-2,2'-furan];
  (1R*,2R*,4'S*,5S*,6R*)-2',3',4',5'-tetrahydro-4'-(2-methoxy-5-trifluoromethoxyphenyl)-1-phenyl-6-phenylsulphonylspiro[8-azabicyclo[3.2.1]octane-2,2'-furan];

(1R*,2R*,4'S*,5S*)-4'-(2-cyclopropyloxy-5-trifluoromethoxyphenyl)-2',3',4',5'-tetrahydro-1-phenylspiro[8-azabicyclo[3.2.1]octane-2,2'-furan];

(1R*,2R*,4'S*,5R*)-2',3',4',5'-tetrahydro-4'-(2-isopropoxy-5-trifluoromethoxyphenyl)-1-phenylspiro[8-azabicyclo[3.2.1]octane-2,2'-furan];

(1R*,2R*,4'S*,5R*)-2',3',4',5'-tetrahydro-4'-(2-(2',2'-difluoro)ethoxy-5-trifluoromethoxyphenyl)-1-phenylspiro[8-azabicyclo[3.2.1]octane-2,2'-furan];

(1R*,2R*,4'S*,5R*)-2',3',4',5'-tetrahydro-1-phenyl-4'-[2-(2,2,2-trifluoroethoxy)-5-trifluoromethoxyphenyl)spiro[8-azabicyclo[3.2.1]octane-2,2'-furan];

(1R*,2R*,4'S*,5R*)-4'-[2-(2-Fluoroethoxy)-5-trifluoromethoxyphenyl]-2',3',4',5'-tetrahydro-1-phenylspiro[8-azabicyclo[3.2.1]octane-2,2'-furan];

(1R*,2R*,4'S*,5S*)-2',3',4',5'-tetrahydro-4'-[(2RS)-2,3-dihydro-2-methyl-5-trifluoromethoxybenzofuran-7-yl]-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(morpholin-1-ylcarbonyl)-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(3-methoxypropylaminocarbonyl)-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(3-methoxypropylaminocarbonyl)-8-methyl-1-phenylspiro[8-azabicyclo[3.2.1]octane-2,2'-furan]; and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of formula (I) and (Ia) will have the stereochemistry of the 1, 2, 4' and 5 positions as possessed by, for instance, the compound of Example 11, i.e. as shown in formula (Ib)

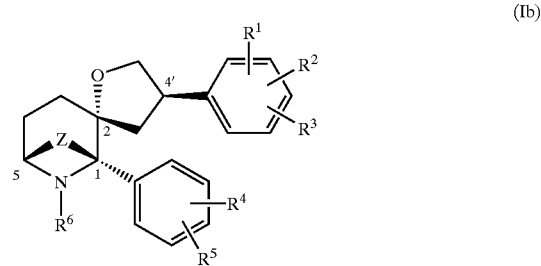

(Ib)

It will be appreciated that the preferred definitions of the various substituents recited herein may be taken alone or in combination and, unless otherwise stated, apply to the generic formula for compounds of the present invention as well as to the preferred class of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

As used herein, the term "treatment" includes prophylactic use to prevent the occurrence or recurrence of any of the aforementioned conditions.

According to a general process (A), compounds of formula (I) may be prepared by the reaction of a compound of formula (II)

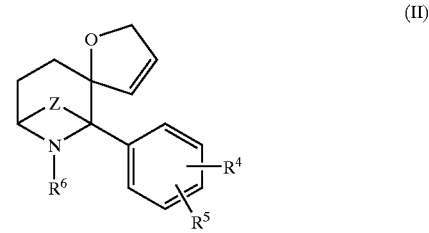

and a compound of formula (III)

where Hal is chlorine, bromine or, preferably, iodine, by a reductive Heck reaction using a palladium catalyst such as palladium acetate with, for example, tri-o-tolylphosphine, dimethylformamide and tributylamine, or tetrabutylammonium chloride and dimethylformamide, and a reducing agent, preferably formic acid or a salt thereof, such as potassium formate.

According to another general process (B), compounds of formula (I) may be prepared by the reaction of a compound of formula (IV)

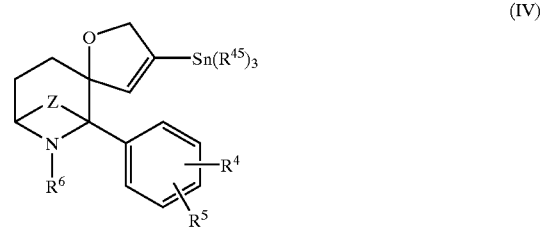

wherein each $R^{45}$ is a $C_{1-4}$alkyl group, preferably methyl or n-butyl groups, with a compound of formula (V)

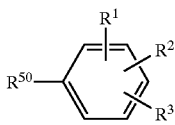

wherein $R^{50}$ is a leaving group such as triflate (—$OSO_2CF_3$) or a halogen atom, for example, chlorine, bromine or iodine, especially triflate, bromine or iodine.

The reaction is conveniently effected in the presence of lithium chloride and a transition metal catalyst such as triphenylphosphine palladium (0). Suitable solvents for the reaction include an aromatic hydrocarbons, for example, toluene, polar aprotic solvents, for example, dimethylformamide, or ethers, for example, dioxan, the reaction being effected at a temperature between 80° C. and the reflux temperature of the solvent. Subsequent reduction of the double bond is effected using the conditions of general process (G), below.

According to another general process (C), compounds of formula (I) may be prepared by the reduction of a compound of formula (VI)

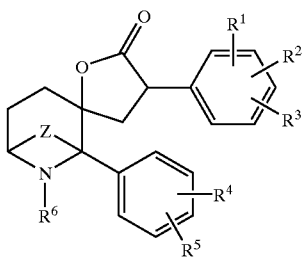

using, for example, a borohydride such as lithium borohydride or lithium triethylborohydride in tetrahydrofuran, or a hydride such as lithium aluminium hydride or diisobutylaluminium hydride.

According to another general process (D), compounds of formula (I) wherein $R^1$ is $C_{1-6}$alkoxy, fluoro$C_{1-6}$alkoxy, $C_{2-6}$alkenoxy, $C_{3-7}$cycloalkoxy, $C_{3-7}$cycloalkyl$C_{1-4}$alkoxy or benzyloxy, may be prepared by the interconversion of a compound of formula (I) wherein $R^1$ is hydroxy, hereinafter referred to as formula (VII)

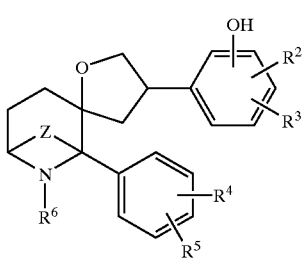

by reaction with an appropriate alkyl-, fluoroalkyl-, alkenyl-, cycloalkyl-, cycloalkylalkyl- or aralkyl-halide, especially the iodide, in the presence of a base.

Suitable bases include alkali metal hydrides, such as sodium hydride, in a suitable solvent such as dimethylformamide. The reaction is conveniently effected at about room temperature.

According to another general process (E), compounds of formula (I) may be prepared by the interconversion of a corresponding compound of formula (I) in which $R^6$ is H, hereinafter referred to as formula (VIII)

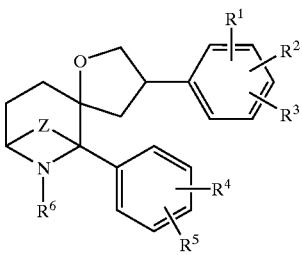

by reaction with a compound of formula (IX):

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group $R^6$ are described, for instance, in International Patent Specification No. WO 95/18124.

According to another general process (F), compounds of formula (I) may be prepared from a compound of formula (X)

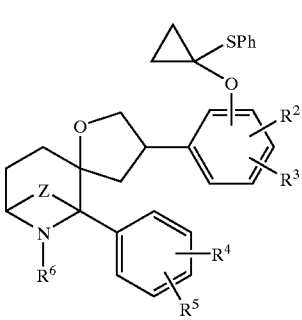

by either
(a) reaction with lithium naphthalenide in tetrahydrofuran, the reaction being effected at reduced temperature, for example at about −78° C.; or
(b) in a first step, oxidation of the phenylthio moiety using, for example, oxone in the presence of aluminium oxide, the reaction being effected in a suitable solvent such as a halogenated hydrocarbon, for example, chloroform, and conveniently at room temperature, and in a second step, removal of the phenylsulfonyl moiety using, for example, sodium amalgam in the presence of disodium hydrogen orthophosphate, the reaction being effected in a suitable solvent such as an alcohol, for example, methanol, and at a reduced temperature, for example, between 0° C. and 10° C.

According to another general process (G), compounds of formula (I) may be prepared by the reduction of a compound of formula (XI)

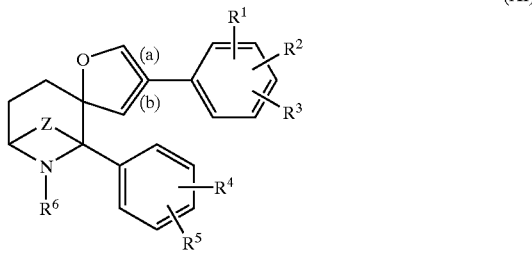
(XI)

wherein the dotted line represents a double bond at either bond (a) or bond (b).

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or reduction using trifluoroacetic acid and triethylsilane.

Further details of suitable procedures will be found in the accompanying Examples.

Compounds of formula (II) may prepared, for example, by the conversion of a stannane of formula (IV) to the corresponding iodide by treatment with iodine at reduced temperature, for example, at about −78° C., in a suitable solvent such as dichloromethane. The iodine may then be displaced to give the compound of formula (II) by treatment with, for example, α,α'-azo-isobutyronitrile and tributyltin hydride in a suitable solvent, for example, toluene, at an elevated temperature, for example, at about 100° C.

Alternatively, compounds of formula (II) may be prepared by the cyclization of a compound of formula (XII)

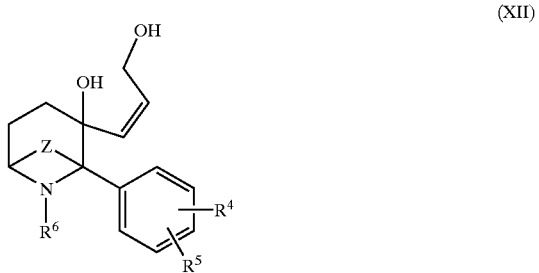
(XII)

using triphenylphosphine and diethylazodicarboxylate in a suitable solvent such as tetrahydrofuran.

Compounds of formula (XII) may be prepared by the partial reduction of an acetylene compound of formula (XIII)

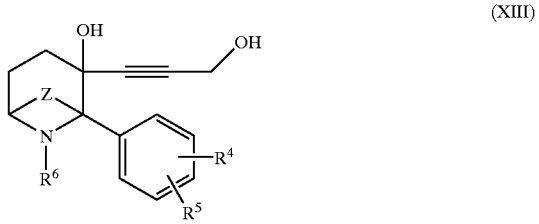
(XIII)

The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Compounds of formula (XIII) may be prepared from compounds of formula (XIV)

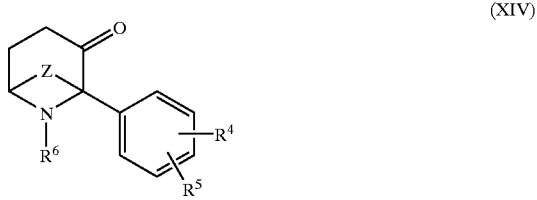
(XIV)

and, for example, a Grignard reagent prepared from O-trimethylsilylpropargyl alcohol using conventional methodology, followed by removal of the hydroxy protecting group.

Compounds of formula (IV) may be prepared from a compound of formula (XIII) by reaction with a compound of the formula $(R^{45})_3SnH$, for example tri-(n-butyl)stannane in the presence of a transition metal catalyst such as tetrakis (triphenylphosphine)palladium(0) in a suitable solvent such as an ether, for example, tetrahydrofuran, followed by a dehydration step using, for example, triphenylphosphine and diethylazodicarboxylate in a suitable solvent such as an ether, for example, tetrahydrofuran.

Alternatively, compounds of formula (IV) may be prepared from a compound of formula (XV)

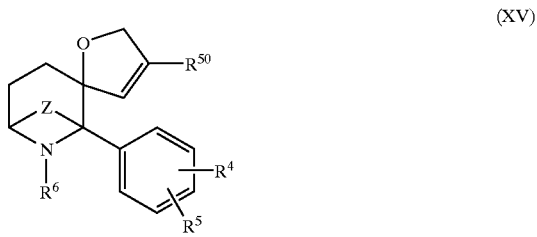
(XV)

wherein $R^{50}$ is as previously defined (and is preferably a triflate group or a bromine or iodine atom), by reaction with a compound of the formula $(R^{45})_3Sn—Sn(R^{45})_3$, for example, hexamethyl distannane. The reaction is conveniently effected in the presence of a base, for example, lithium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (XV) may be prepared from a compound of formula (XX) by enolisation of the ketone in the presence of a base, for example, sodium hexamethyldisilazide, followed by reaction with a reagent capable of introducing a suitable leaving group, for instance, where $R^{50}$ is $—OSO_2CF_3$, using 2-[N,N-bis (trifluoromethylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (VI) may be prepared by reduction of a compound of formula (XVI)

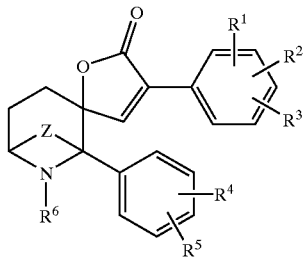

(XVI)

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or reduction using trifluoroacetic acid and triethylsilane.

Compounds of formula (XVI) may be prepared from a compound of formula (XVII)

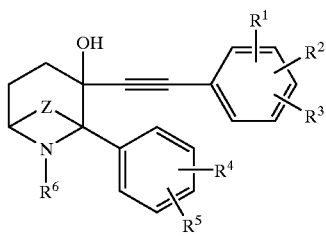

(XVII)

by a three-step process. Fierily, the compound of formula (XVII) is reduced using, for example, Red-Al™ in a suitable aprotic solvent such as an aromatic hydrocarbon, for example, toluene, or an ether, for example, diethyl ether, or a mixture thereof. The resultant compound is then iodinated using iodine. Finally cyclisation takes place by reaction with carbon monoxide in the presence of a transition metal catalyst such as tris(dibenzylidineacetone)palladium(0) and 1,4-bis(diphenylphosphino)butane, and an organic base such as a trialkylamine, for example, isopropyldiethylamine. The cyclisation is conveniently effected in an aprotic solvent such as an ether, for example, tetrahydrofuran.

Compounds of formula (XVII) may be prepared by the reaction of a compound of formula (XIV) with a compound of formula (XVIII)

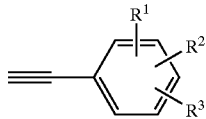

(XVIII)

The reaction is conveniently effected in the presence of ethyl magnesium bromide in a suitable aprotic solvent such as an ether, for example, tetrahydrofuran.

Compounds of formula (X) may be prepared from a compound of formula (VII) by reaction with (1-iodo-cycloprop-1-yl)phenylsulfide.

Compounds of formula (XI) may be prepared by the dehydration of a compound of formula (XIX)

(XIX)

using an acid such as trifluoroacetic acid. The reaction is conveniently effected at a temperature between 0° C. and room temperature, using a suitable organic solvent such as a halogenated hydrocarbon, for example, dichloromethane.

Compounds of formula (XIX) may be prepared by the reaction of a compound of formula (XX)

(XX)

with a Grignard reagent prepared from a compound of formula (III), preferably using magnesium and a bromide of formula (III). The coupling reaction is conveniently effected at reduced temperature, for example, at about 0° C., using a suitable solvent such as an ether, for example, diethyl ether.

Compounds of formula (XX) may be prepared from a compound of formula (XIV) by a variety of processes, for instance, by the following reaction sequence (Scheme A) or by methods analogous thereto:

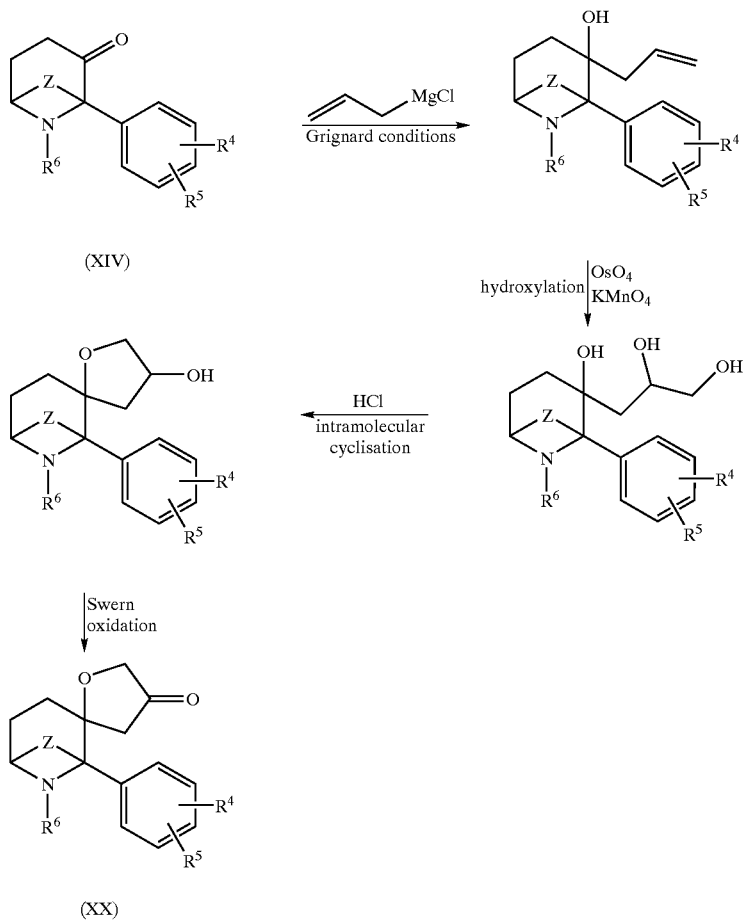

(XIV)

(XX)

Compounds of formula (XIV) may be prepared from a compound of formula (XXI)

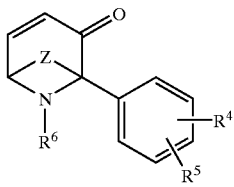

(XXI)

by catalytic hydrogenation using a metal catalyst such as palladium or platinum or hydroxides or oxides thereof, preferably in a suitable solvent such as alcohol, for example, methanol or ethanol, or an ester, for example, ethyl acetate, or an organic acid, for example, acetic acid, or a mixture thereof.

Compounds of formula (XI) wherein $R^6$ is benzyl or allyl, may be prepared from a compound of formula (XXII)

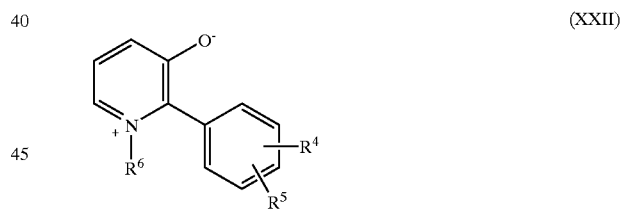

(or a corresponding compound wherein the $O^-$ is OH, and the compound is associated with a counterion, such as a bromide or chloride ion) by reaction with a vinyl compound of the formula $R^9CH=CH_2$, in particular where $R^9$ is cyano, $SO_2R^{13}$ (especially where $R^{13}$ is phenyl) or $CO_2R^{13}$ (especially where $R^{13}$ is tert-butyl), in the presence of an organic base such as a trialkylamine, for example, triethylamine. The reaction is conveniently effected in an aprotic solvent such as an aromatic hydrocarbon, for example, toluene.

The reaction of a compound of formula (XXII) with acrylonitrile is particularly suitable for preparing compounds where the $R^9$ substituent is situated on either of the carbon atoms of the two-carbon bridge.

Where they are not commercially available, the intermediates of formula (II), (IV) and (XVIII) above may be prepared, for example, from the corresponding phenol derivative using, for example, the procedures described in the accompanying Examples, or by alternative procedures which will be readily apparent to one skilled in the art.

In a preferred embodiment of the aforementioned processes, $R^6$ is a benzyl group. The various reduction reactions described above may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (IX) and (XXII) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the human $NK_1$ receptor of less than 100 nM on said test method.

The following non-limiting Examples serve to illustrate the preparation of compounds of the present invention:

DESCRIPTION 1

O-Vinyloxy-4-trifluoromethoxybenzene

Diethyl azodicarboxylate (19 ml, 121 mmol) was added dropwise to a stirred solution of 4-trifluoromethoxyphenol (20.5 g, 115 mmol), triphenylphosphine (31.5 g, 120 mmol) and 2-bromoethanol (10 ml, 141 mmol) at +5° C. The cold bath was removed and the reaction mixture was stirred at ambient temperature for 20 hours and concentrated in vacuo. The residue was treated with diethyl ether (50 ml) followed by hexane (200 ml). The solid was filtered off and the filtrate was concentrated. The residue was treated with dichloromethane (150 ml) followed by 50% aqueous NaOH (150 ml) and tetra-n-butylammonium hydrogen sulphate (40 g, 118 mmol). The mixture was stirred at room temperature for 3 hours, diluted with water (200 ml) and layers were separated. The aqueous phase was extracted into diethyl ether. The combined organic extracts were washed with water, dried ($Na_2SO_4$) and concentrated under atmospheric pressure using a Vigreux column (300 mm). The residue was distilled under reduced pressure to give the title compound (9.64 g, 41%, bp. 64° C./20 mm Hg) as a colourless liquid.
$\delta_H$ (250 MHz, $CDCl_3$): 7.17 (2H, m), 7.01 (2H, m), 6.60 (1H, dd, J 6.1 Hz, 13.7 Hz), 4.79 (1H, dd, J 1.8 Hz, 13.7 Hz), 4.48 (1H, dd, J 1.8 Hz, 6.0 Hz).

DESCRIPTION 2

O-Cyclopropyloxy-4-trifluoromethoxybenzene

Diethyl zinc (24 ml, neat, 235 mmol) was added dropwise to a stirred solution of O-vinyloxy-4-trifluoromethoxybenzene (Description 1; 9.6 g, 47 mmol), diiodomethane (37.7 ml, 470 mmol) in dimethoxyethane (200 ml) over 30 minutes. The reaction mixture was heated at reflux for 13 hours, cooled to room temperature and quenched with saturated aqueous ammonium chloride. The layers were separated and the upper aqueous phase was extracted into hexane (2×50 ml). The combined organic extracts were washed with water and brine, dried ($Na_2SO_4$) and concentrated under atmospheric pressure using a Vigreux column (300 mm). The residue was distilled under reduced pressure to give the title compound (6.7 g, 65%) as a colourless liquid.
$\delta_H$ (250 MHz, $CDCl_3$): 7.13 (2H, m), 7.01 (2H, m), 3.70 (1H, m), 0.77 (4H, m).

DESCRIPTION 3

2-Cyclopropyloxy-5-trifluoromethoxybenzaldehyde

A of solution of tert-butyl lithium in pentane (1.7M, 30 ml, 51 mmol) was added dropwise to a stirred solution of O-cyclopropyloxy-4-trifluoromethoxybenzene (Description 2; 5.2 g, 23.7 mmol) in tetrahydrofuran (50 ml) at −78° C. over 10 minutes. The mixture was stirred for 30 minutes at −78° C. and DMF (8 ml) was added dropwise. The reaction mixture was warmed to 0° C. over 90 minutes, quenched with saturated aqueous ammonium chloride and extracted into hexane (3×30 ml). The combined organic extracts were dried ($Na_2SO_4$) and concentrated. The residue was purified by chromatography on silica gel (iso-hexane:diethyl ether 0–10%) to give the title compound (4.59 g, 84%) as a solid.
$\delta_H$ (250 MHz, $CDCl_3$): 10.35 (1H, m), 7.67 (1H, m), 7.40 (2H, m), 3.87 (1H, m), 0.87 (4H, m).

DESCRIPTION 4

2-Cyclopropyloxy-5-trifluoromethoxyphenylethyne

Potassium carbonate (6.15 g, 44 mmol) was added to a stirred solution of 2-cyclopropyloxy-5-trifluoromethoxybenzaldehyde (Description 3; 4.4 g, 17.8 mmol), and acetyl diazomethyl phosphonate (6.15 g, 32 mmol) in dry methanol (50 ml) at +5° C. The reaction mixture was stirred at +5° C. for 30 minutes and at room temperature for 3.5 hours. The mixture was quenched with saturated aqueous ammonium chloride and extracted into hexane (3×30 ml). The combined organic extracts were dried ($Na_2SO_4$) and concentrated. The residue was purified by chromatography on silica gel (iso-hexane:diethyl ether 0–45%) to give the title compound (4.2 g, 94%).
$\delta_H$ (250 MHz, $CDCl_3$): 7.31 (1H, d, J 2.7 Hz), 7.24 (1H, d, J 9.0 Hz), 7.18 (1H, ddd, J 0.7 Hz, 1.7 Hz, 9.1 Hz), 3.80 (1H, m), 3.30 (1H, s), 0.85 (4H, m).

DESCRIPTION 5

N-Benzyl-3-hydroxy-2-phenylpyridinium Bromide

A suspension of 3-hydroxy-2-phenylpyridine (20 g, 116 mmol) in toluene (250 ml) was heated at reflux for 30 minutes. Benzyl bromide (20 ml) was added and the reaction mixture was heated at reflux for 6 hours then cooled using an ice bath. The solid residue was collected by filtration and washed twice with ether to give crude N-benzyl-3-hydroxy-2-phenylpyridinium bromide (36.5 g, 91%) which was used in the next step without further purification.
$\delta_H$ (360 MHz, $CDCl_3$): 11.88 (1H, s), 9.47 (1H, d, J 7.2 Hz), 8.16 (1H, d, J 8.1 Hz), 8.05 (1H, dd, J 6.0 Hz, 8.8 Hz), 7.60–7.45 (3H, m), 7.37–7.22 (5H, m), 6.88 (2H, dd, J 6.2 Hz, 7.9 Hz), 5.61 (2H, s).

DESCRIPTION 6

(1R*,5S*,6R*)-8-Benzyl-1-phenyl-6-phenylsulphonyl-8-azabicyclo[3.2.1]oct-3-en-2-one A mixture of N-benzyl-3-hydroxy-2-phenylpyridinium bromide (Description 5; 4.91 g, 14.3 mmol), phenyl vinyl sulphone (4.2 g, 25 mmol), triethylamine (2.8 ml, 20 mmol) and 1,4-dioxane (50 ml) was heated at reflux overnight. After cooling to room temperature, the reaction mixture was poured onto saturated aqueous $NaHCO_3$ and extracted with ethyl acetate (3×100 ml). The combined organic extracts were dried ($Na_2SO_4$) and concentrated. The residue was purified by chromatography on silica gel (iso-hexane:diethyl ether 10–70%) to give the title compound (4.84 g, 78%) as a yellow-orange foam. Crystallisation from iso-hexane:diethyl ether gave the product as yellow rhombs.

$\delta_H$ (360 MHz, $CDCl_3$): 7.75–7.60 (5H, m), 7.48 (2H, t, J 7.7 Hz), 7.41–7.25 (8H, m), 6.86 (1H, dd, J 4.8 Hz, 9.6 Hz), 6.23 (1H, d, J 9.6 Hz), 4.25 (1H, d, J 4.8 Hz), 3.65 (1H, d, J 13.4 Hz), 3.56 (1H, dd, J 4.0 Hz, 9.4 Hz), 3.43 (1H, d, J 13.5 Hz), 2.83 (1H, dd, J 3.9 Hz, 14.9 Hz), 2.56 (1H, dd, J 9.4 Hz, 15.0 Hz).

DESCRIPTION 7

(1R*,5S*,6R*)-8-Benzyl-1-phenyl-6-phenylsulphonyl-8-azabicyclo[3.2.1]octan-2-one 10% Palladium on carbon (1 g) was added as a slurry in water (2 ml) to a solution of (1R*,5S*,6R*)-8-benzyl-1-phenyl-6-phenylsulphonyl-8-azabicyclo[3.2.1]oct-3-ene-2-one (Description 6; 11 g, 25.6 mmol) in methanol (50 ml) and ethyl acetate (50 ml). The mixture was hydrogenated at 30 psi for one hour. The reaction mixture was filtered through a pad of Celite™. The filter cake was washed with dichloromethane (1L) and the combined filtrates concentrated in vacuo to give the title compound (10.8 g, 98%).

$\delta_H$ (400 MHz, $CDCl_3$): 7.79 (2H, d, J 7.2 Hz), 7.68 (1H, t, J 6.4 Hz), 7.51 (2H, t, J 7.6 Hz), 7.41–7.25 (10H, m), 3.94 (1H, br s), 3.73–3.69 (1H, d, J 14.0 Hz), 3.63 (1H, t, J 7.7 Hz), 3.36 (1H, d, J 14.0 Hz), 2.71–2.54 (5H, m), 1.77 (1H, m).

DESCRIPTION 8

(1R*,2S*,5S*,6R*)-8-Benzyl-2-(2-cyclopropyloxy-5-trifluoromethoxyphenyl)ethynyl-1-phenyl-6-phenylsulphonyl-8-azabicyclo[3.2.1]octan-2-ol A solution of n-butyl lithium in hexanes (1.6M, 5 ml, 8 mmol) was added dropwise to a stirred solution of 2-cyclopropyloxy-5-trifluoromethoxyphenylethyne (Description 4; 2.0 g, 8.2 mmol) in tetrahydrofuran (30 ml) at –78° C. to form an orange solution that turned violet at the end of addition. The mixture was stirred for 10 minutes and solid anhydrous cerium(III) chloride (2 g, 8.1 mmol) was added. The mixture was stirred for 30 minutes at –78° C. and a solution of (1R*,5S*,6R*)-8-benzyl-1-phenyl-6-phenylsulphonyl-8-azabicyclo[3.2.1]octan-2-one (Description 7; 2.9 g, 6.7 mmol) in tetrahydrofuran (25 ml) was added dropwise. The reaction mixture was warmed to 0° C. over 30 minutes, stirred at 0° C. for 15 minutes, quenched with saturated aqueous ammonium chloride and extracted with ethyl acetate (3×100 ml). The combined organic extracts were washed with brine, dried ($Na_2SO_4$) and concentrated. The residue was purified by chromatography on silica gel (iso-hexane:ethyl acetate) to give the title compound (2.4 g, 53%) which was recrystallised from ethyl acetate:iso-hexane.

$\delta_H$ (400 MHz, $CDCl_3$): 7.86 (2H, dm, J 7.2 Hz), 7.71 (2H, dm, J 7.2 Hz), 7.65 (1H, t, J 7.5 Hz), 7.54 (2H, t, J 8.0 Hz), 7.48 (2H, d, J 7.3 Hz), 7.40–7.25 (6H, m), 7.14 (1H, d, J 9.0 Hz), 7.08 (1H, dd, J 2.5 Hz, 9.2 Hz), 7.00 (1H, d, J 2.5 Hz), 4.05 (1H, d, J 14.6 Hz), 3.94 (1H, br s), 3.77 (1H, d, J 14.6 Hz), 3.68 (1H, m), 3.64 (1H, t, J 8.6 Hz), 3.51 (1H, br s), 2.94 (1H, dd, J 9.1 Hz, 14.2 Hz), 2.87 (1H, dd, J 6.7 Hz, 14.2 Hz), 2.21 (1H, m), 2.10 (1H, m), 1.29 (1H, m), 0.76 (2H, m), 0.66 (2H, m).

DESCRIPTION 9

(1R*,2R*,6S*,6R*)-8-Benzyl-2-[(Z)-2-(2-cyclopropyloxy-5-trifluoromethoxyphenyl)-2-iodoethenyl]-1-phenyl-6-phenylsulphonyl-8-azabicyclo[3.2.1]octan-2-ol (1R*,2S*,5S*,6R*)-8-benzyl-2-(2-cyclopropyloxy-5-trifluoromethoxyphenyl)ethynyl-1-phenyl-6-phenylsulphonyl-8-azabicyclo[3.2.1]octan-2-ol (Description 8; 2.4 g, 3.6 mmol) was dissolved in hot, dry toluene (35 ml), cooled to room temperature and treated with diethyl ether (15 ml) followed by a solution of Red-Al® (3.4M in toluene, 1.8 ml, 6.12 mmol). The mixture was stirred at room temperature for 2 hours and at +40° C. for 30 minutes. The reaction mixture was cooled to –60° C. and a solution of iodine (2.5 g, 9.8 mmol) in toluene (35 ml) was added. The cold bath was removed and the mixture was stirred at ambient temperature for 30 minutes, treated with 10% aqueous $Na_2SO_3$ and stirred until for 1 hour. The phases were separated. The aqueous layer was extracted twice with ethyl acetate (2×50 ml). The combined organic extracts were washed with brine, dried ($Na_2SO_4$) and concentrated. The residue was purified by chromatography on silica gel (iso-hexane:ethyl acetate) to give the title compound (1.88 g, 66%).

$\delta_H$ (360 MHz, $CDCl_3$): 7.84 (2H, dm, J 7.1 Hz), 7.70–7.45 (7H, m), 7.40–7.25 (6H, m), 7.05 (1H, d, J 9.0 Hz), 7.01 (1H, dd, J 2.3 Hz, 9.0 Hz), 6.52 (1H, d, J 2.3 Hz), 5.90 (1H, s), 4.25 (1H, s), 4.01 (1H, d, J 14.5 Hz), 3.92 (1H, br s), 3.75 (1H, d, J 14.4 Hz), 3.71 (1H, m), 3.59 (1H, dd, J 7.7 Hz, 9.5 Hz), 2.85 (1H, dd, J 6.7 Hz, 14.0 Hz), 2.59 (1H, dd, J 9.1 Hz, 14.0 Hz), 2.31 (1H, dd, J 4.6 Hz, 14.4 Hz), 2.21 (1H, ddt, J 2.8 Hz, 5.3 Hz, 14.0 Hz), 1.82 (1H, ddd, J 5.2 Hz, 13.6 Hz), 1.34 (1H, m), 0.80–0.65 (4H, m).

DESCRIPTION 10

(1R*,2R*,5S*,6R*)-8-Benzyl-4'-(2-cyclopropyloxy-5-trifluoromethoxyphenyl)-1-phenyl-6-phenylsulphonylspiro[8-azabicyclo[3.2.1]octane-2,2'(5'H)-furan]-5'-one A mixture of (1R*,2R*,5S*,6R*)-8-benzyl-2-[(Z)-2-(2-cyclopropyloxy-5-trifluoromethoxyphenyl)-2-iodoethenyl]-1-phenyl-6-phenylsulphonyl-8-azabicyclo[3.2.1]octan-2-ol (Description 9; 690 mg, 0.86 mmol), 1,4-bis(diphenylphosphino)butane (45 mg, 0.1 mmol), $Pd_2(dba)_3$ (140 mg, 1.5 mmol), ethyl di-iso-propyl amine (0.75 ml) and tetrahydrofuran (20 ml) was stirred under an atmosphere of carbon monoxide (1 atm) at +50° C. for 24 hours. Additional portion of 1,4-bis(diphenylphosphino)butane (45 mg, 0.1 mmol) and $Pd_2(dba)_3$ (140 mg, 1.5 mmol) were added and the mixture was stirred for an additional 24 hours. After cooling to room temperature the mixture was diluted with ethyl acetate and filtered through a pad of Celite™. The filtrate was concentrated and the residue was purified by chromatography on silica gel (iso-hexane:ethyl acetate 0–35%) to give the title compound (350 mg, 58%).

$\delta_H$ (400 MHz, $CDCl_3$): 7.89 (2H, dm, J 8.6 Hz), 7.67 (1H, t, J 7.4 Hz), 7.62–7.53 (4H, m), 7.48 (1H, d, J 2.8 Hz), 7.46 (1H, s), 7.40–7.25 (3H, m), 7.28 (1H, t, J 7.4 Hz), 7.23–7.13 (4H, m), 7.09 (1H, dd, J 2.4 Hz, 9.0 Hz), 3.99 (1H, d, J 14.6

Hz, 3.91 (1H, br s), 3.85 (1H, d, J 14.6 Hz), 3.77 (1H, t, J 8.0 Hz), 3.71 (1H, m), 3.13 (1H, dd, J 7.4 Hz, 14.1 Hz), 2.76 (1H, dd, J 8.9 Hz, 14.0 Hz), 2.25 (1H, ddt, J 2.7 Hz, J 5.5 Hz, 12.5 Hz), 2.04 (1H, dt, J 6.3 Hz, 13.3 Hz), 1.71 (1H, dd, J 5.2 Hz, 15.0 Hz), 1.38 (1H, m).

DESCRIPTION 11

(1R*,2R*,4'R*,5S*,6R*)-2',3',4',5'-Tetrahydro-4'-(2-methoxy-5-trifluoromethoxyphenyl)-1-phenyl-6-phenylsulphonylspiro[8-azabicyclo[3.2.1]octane-2,2'-furan]-5-one A mixture of (1R*,2R*,5S*,6R*)-8-benzyl-2'-(2-cyclopropyloxy-5-trifluoromethoxyphenyl)-1-phenyl-6-phenylsulphonylspiro[8-azabicyclo[3.2.1]octane-2,2'(5'H)-furan]-5'-one (Description 10; 349 mg, 0.5 mmol), 5% palladium on charcoal (1 g, 1 mmol) and ethanol (20 ml) was stirred under hydrogen (1 atm) at +650° C. for 2.5 hours. The reaction mixture was cooled to room temperature, flushed with nitrogen gas and filtered through a pad of Celite™. The filtrate was concentrated and purified by flash chromatography to give a mixture of phenol and n-propyl derivative in ratio 3.4:1. The mixture was treated with dry tetrahydrofuran (3 ml) followed by diethyl azodicarboxylate (0.15 ml, 0.95 mmol), triphenylphosphine (293 mg, 1.1 mmol) and methanol (0.2 ml) and stirred at room temperature for 1 hour. The mixture was quenched with water (1 drop) and concentrated. The residue was purified by chromatography on silica gel (iso-hexane:ethyl acetate 0–100%) to give the title compound (180 mg, 61%).

$\delta_H$ (360 MHz, CDCl$_3$): 7.89 (2H, dm, J 8.2 Hz), 7.60–7.40 (6H, m), 7.35 (2H, m), 7.41–7.35 (4H, m), 6.97 (1H, dd, J 2.7 Hz, 9.0 Hz), 6.67 (1H, d, J 9.0 Hz), 5.88 (1H, d, J 2.8 Hz), 4.09 (1H, t, J 10.6 Hz), 4.07 (1H, s), 3.67 (1H, dd, J 5.3 Hz, 8.5 Hz), 3.49 (3H, s), 2.60 (1H, dd, J 5.4 Hz, 14.5 Hz), 2.49 (1H, dd, J 8.6 Hz, 14.5 Hz), 2.25–2.10 (3H, m), 1.60 (1H, m), 1.51 (1H, m).

DESCRIPTION 12

(1R*,2R*,4'S*,5S*,6R*)-2',3',4',5'-Tetrahydro-4'-(2-methoxy-6-trifluoromethoxyphenyl)-1-phenyl-6-phenylsulphonylspiro[8-azabicyclo[3.2.1]octane-2,2'-furan]-5-one 1,8-Diazabicyclo[5.4.0]-undec-7-ene (0.05 ml, 0.34 mmol) was added to a solution of (1R*,2R*,4'R*,5S*,6R*)-2',3',4',5'-tetrahydro-4'-(2-methoxy-5-trifluoromethoxyphenyl)-1-phenyl-6-phenylsulphonylspiro[8-azabicyclo[3.2.1]octane-2,2'-furan]-5-one (Description 11; 150 mg, 0.26 mmol) in dichloromethane (2 ml). A white precipitate formed. The mixture was stirred at room temperature overnight, then treated with hexane (2 ml) and cooled to −20° C. The solid was filtered off to give the title compound (100 mg, 66%) as white crystals.

$\delta_H$ (400 MHz, CDCl$_3$): 7.91 (2H, dm, J 7.2 Hz), 7.68 (1H, t, J 7.6 Hz), 7.58 (2H, t, J 7.8 Hz), 7.51 (2H, m), 7.42 (3H, m), 7.03 (1H, dd, J 2.1 Hz, 8.9 Hz), 6.74 (1H, d, J 9.0 Hz), 6.55 (1H, d, J 2.5 Hz), 4.07 (1H, br s), 3.73 (3H, s), 3.64 (1H, dd, J 5.3 Hz, 8.5 Hz), 2.65 (1H, dd, J 5.3 Hz, 14.5 Hz), 2.58 (1H, dd, J 8.6 Hz, 14.5 Hz), 2.24 (1H, dd, J 8.3 Hz, 11.0 Hz), 2.20 (1H, m), 2.00 (1H, dd, J 5.4 Hz, 14.9 Hz), 1.89–1.77 (2H, m), 1.65 (1H, dt, J 7.0 Hz, 14.2 Hz), 1.49 (1H, m).

DESCRIPTION 13

(1R*,2R*,5S*,6R*)-8-Benzyl-2-(3-hydroxypropynyl)-1-phenyl-6-phenylsulphonyl-8-azabicyclo[3.2.1]octan-2-ol A solution of n-butyl lithium in hexanes (1.6M, 20 ml, 32 mmol) was added to a stirred, −78° C. solution of O-trimethylsilylpropargyl alcohol (5 ml, 34.8 mmol) in tetrahydrofuran (50 ml). After 30 minutes a solution of (1R*,5S*,6R*)-8-benzyl-1-phenyl-6-phenylsulphonyl-8-azabicyclo[3.2.1]octan-2-one (Description 7; 4.6 g, 10.7 mmol) in tetrahydrofuran (20 ml) was added. The mixture was stirred for 30 minutes then quenched by addition of saturated ammonium chloride. The mixture was diluted with ethyl acetate and washed (2×100 ml) with water. The organic layer was separated and treated with a solution of tetrabutylammonium fluoride (11.5 ml, 1.0M solution in tetrahydrofuran) for 20 minutes at room temperature. The solution was washed with water (2×100 ml) then dried (MgSO$_4$), filtered and concentrated in vacuo. The residue was chromatographed on silica gel eluting with 1:1, 3:2 and 2:1 ethyl acetate/iso-hexanes to yield the title compound (4.12 g, 79%).

$\delta_H$ (400 MHz, CDCl$_3$): 7.86 (2H, d, J 7.2 Hz), 7.63–7.53 (5H, m), 7.45 (2H, d, J 7.2 Hz), 7.38–7.26 (6H, m), 4.07 (2H, s), 4.01 (1H, d, J 14.6 Hz), 3.93 (1H, s), 3.77 (1H, s), 3.73 (1H, d, J 14.4 Hz), 3.6 (1H, m), 2.86–2.81 (2H, m), 2.10–1.96 (3H, m).

DESCRIPTION 14

(1R*,2R*,5S*,6R*)-8-Benzyl-2-[(Z)-3-hydroxypropenyl]-1-phenyl-6-phenylsulphonyl-8-azabicyclo[3.2.1]octan-2-ol Lindlar catalyst (200 mg) was added to a solution of (1R*,2R*,5S*,6R*)-8-benzyl-2-(3-hydroxypropynyl)-1-phenyl-6-phenylsulphonyl-8-azabicyclo[3.2.1]octan-2-ol (Description 13; 2.1 g, 4.3 mmol) in ethyl acetate (100 ml). The mixture was stirred at room temperature for 8 hours then filtered through Celite™ and the filtrate concentrated in vacuo to yield the title compound (1.88 g, 90%).

$\delta_H$ (400 MHz, CDCl$_3$): 7.89 (2H, d, J 7.2 Hz), 7.70 (1H, m), 7.58 (2H, m), 7.47 (2H, m), 7.39–7.24 (8H, m), 5.35 (1H, m), 5.20 (1H, d, J 14.4 Hz), 4.91 (1H, br s), 4.00 (1H, d, J 14.4 Hz), 3.96 (1H, br s), 3.83 (1H, d, J 14.4 Hz), 3.77–3.63 (3H, m), 2.95 (1H, dd, J 14.0 Hz, 7.4 Hz), 2.66 (1H, dd, J 9.2 Hz, 4.9 Hz), 2.01 (1H, m), 1.84 (1H, dd, J 5.0 Hz), 1.65 (1H, td, J 5.8, 5.0 Hz), 1.39 (1H, m).

DESCRIPTION 15

(1R*,2R*,5S*,6R*)-8-Benzyl-2',5'-dihydro-1-phenyl-6-phenylsulfonylspiro[8-azabicyclo[3.2.1]octane-2,2'-furan]

Diethylazodicarboxylate, 0.7 ml, 4.4 mmol was added dropwise to a +5° C. solution of (1R*,2R*,5S*,6R*)-8-benzyl-2-[(Z)-3-hydroxypropenyl]-1-phenyl-6-phenylsulphonyl-8-azabicyclo[3.2.1]octan-2-ol (Description 14; 1.8 g, 3.7 mmol) and triphenylphosphine (1.15 g, 4.4 mmol) in tetrahydrofuran (25 ml). After 90 minutes the mixture was diluted with ethyl acetate and washed (×2) with water (100 ml). The organic extracts were separated, dried (MgSO$_4$), filtered and concentrated in vacuo. The residue was chromatographed on silica gel eluting with 10, 20, 30 and 50% ethyl acetate/iso-hexanes to yield the title compound (1.48 g, 86%).

$\delta_H$ (400 MHz, CDCl$_3$): 7.86 (2H, d, J 7.9 Hz), 7.65–7.51 (6H, m), 7.35–7.18 (7H, m 5.57 (2H, br s), 4.55 (1H, d, J 14.2 Hz), 4.25 (1H, d, J 14.6 Hz), 3.91 (1H, d, J 16.3 Hz), 3.83 (1H, s), 3.69 (1H, d, J 16.2 Hz), 3.64 (1H, m), 2.88 (1H, dd, J 7.8 Hz, 15.5 Hz), 2.5 (1H, dd, J 10.1 Hz, 15.5 Hz), 2.18 (1H, m), 1.69 (2H, m).

DESCRIPTION 16

(1R*,2R*,4'S*,5S*,6R*)-8-Benzyl-4'-(2-benzyloxy-5-trifluoromethoxyphenyl)-2',3',4',5'-tetrahydro-1-phenyl-6-phenylsulfonylspiro[8-azabicyclo[3.2.1]octane-2,2'-furan]

Palladium acetate (140 mg, 0.6 mmol) was added to a degassed suspension of (1R*,2R*,5S*,6R*)-8-benzyl-2',5'- dihydro-1-phenyl-6-phenylsulfonylspiro[8-azabicyclo[3.2.1]octane-2,2'-furan] (Description 15; 2.9 g, 6.15 mmol), 2-benzyloxy-5-trifluoromethoxyiodobenzene (7.3 g, 18.5 mmol), tetrabutylammonium chloride, (1.7 g, 6.15 mmol), lithium chloride (2.6 g, 62 mmol), triethylamine (2.6 ml, 18 mmol), potassium formate (1.56 g, 18.5 mmol), N,N-dimethylformamide (40 ml) and water (3 ml). The mixture was stirred at 60° C. for 72 hours then partitioned between brine and ethyl acetate. The organic layer was washed (×3) with water then dried (MgSO$_4$), filtered and concentrated in vacuo. The residue was chromatographed on silica gel eluting with 5, 10, 15 and 30% ethyl acetate/iso-hexanes to yield the title compound (2.0 g, 44%).

$\delta_H$ (400 MHz CDCl$_3$): 7.89 (2H, d, J 7.4 Hz), 7.65 (1H, t J 5.6 Hz), 7.63–7.53 (3H, m), 7.44–7.39 (4H, m), 7.33–7.20 (7H, m), 7.11 (3H, m), 6.94 (1H, dd, J 2.2 Hz, 8.7 Hz), 6.73–6.70 (2H, m), 4.86 (2H, AB system), 3.99 (1H, t, J 7.6 Hz), 3.86–3.83 (2H, m), 3.71–3.65 (2H, m), 3.55 (1H, dd, J 8.1 Hz, 10.9 Hz), 2.89 (1H, dd, J 7.6 Hz, 13.7 Hz), 2.35 (1H, dd, J 9.0 Hz, 13.7 Hz), 2.12–2.04 (2H, m), 1.82 (1H, dd, J 5.0 Hz, 14.8 Hz), 1.72–1.42 (3H, m), 1.31–1.28 (1H, m).

DESCRIPTION 17

(1R*,2R*,4'S*,5S*,6R*)-2',3',4',5'-Tetrahydro-4'-[2-(1-phenylthiocyclopropyloxy)-5-trifluoromethoxyphenyl]-1-phenyl-6-phenylsulphonylspiro[8-azabicyclo[3.2.1]octane-2,2'-furan]

The mixture of (1R*,2R*,4S*,5S*,6R*)-2',3',4',5'-tetrahydro-4'-(2-hydroxy-5-trifluoromethoxyphenyl)-1-phenyl-6-phenylsulphonylspiro[8-azabicyclo[3.2.1]octane-2,2'-furan] (Example 10; 315 mg, 0.56 mmol), 1-iodo-1-phenylthiocyclopropane (1.8 g, 6.5 mmol), silver carbonate (1.03 g, 3.7 mmol) and toluene (7 ml) was stirred at +40° C. for 2 hours. The reaction mixture was cooled to room temperature and filtered through a pad of Celite™. The filtrate was concentrated and purified by chromatography on silica gel (iso-hexane:ethyl acetate) to give the title compound (245 mg, 62%).

$\delta_H$ (400 MHz, CDCl$_3$): 7.91 (2H, dm, J 7.9 Hz), 7.68 (1H, m), 7.59 (2H, m), 7.43–7.20 (4H, m), 7.13 (1H, d, J 9.0 Hz), 7.00 (1H, dd, J 2.6 Hz, 9.0 Hz), 6.77 (1H, d, J 2.5 Hz), 4.03 (1H, br s), 3.70 (1H, t, J 7.7 Hz), 3.62 (1H, dd, J 5.2 Hz, 8.6 Hz), 3.41 (1H, dd, J 8.3 Hz, 10.7 Hz), 2.51 (1H, dd, J 5.2 Hz, 14.3 Hz), 2.46 (1H, dd, J 8.7 Hz, 14.3 Hz), 2.16 (1H, dd, J 8.0 Hz, 12.8 Hz), 2.11 (1H, m), 1.88 (1H, m), 1.85–1.20 (3H, m).

DESCRIPTION 18

(1R*,2R*,5S*,6R*)-8-Benzyl-2',5'-dihydro-1-phenyl-6-phenylsulfonyl-4'-tributylstannylspiro[8-azabicyclo[3.2.1]octane-2,2'-furan]

Tetrakis(triphenylphosphine)palladium(0) (300 mg, 0.26 mmol) was added to a degassed solution of (1R*,2R*,5S*,6R*)-8-benzyl-2-(3-hydroxypropynyl)-1-phenyl-6-phenylsulphonyl-8-azabicyclo[3.2.1]octan-2-ol (Description 13; 1.8 g, 3.7 mmol) in tetrahydrofuran (50 ml). The mixture was cooled to +5° C. before tri-n-butyltin hydride (1.3 g, 4.4 mmol) was added. The mixture was allowed to warm to room temperature and stirred for a further 18 hours before triphenylphosphine (1 g, 3.7 mmol) and diethyl azodicarboxylate (0.65 g, 3.7 mmol) were added. After 3 hours the mixture was concentrated in vacuo. The residue was chromatographed on silica gel eluting with 5 and 10% ethyl acetate/iso-hexanes to give the title compound (154 mg, 5.5%).

$\delta_H$ (400 MHz, CDCl$_3$): 7.83 (2H, d, J 7.9 Hz), 7.64 (1H, t, J 7.4 Hz), 7.61–7.49 (6H, m), 7.33 (2H, t, J 7.4 Hz), 7.23–7.14 (4H, m), 5.57 (1H, t, J 2.2 Hz), 4.63 (1H, dd, J 2.2 Hz, 13.2 Hz), 4.35 (1H, dd, J 2.2 Hz, 13.2 Hz), 3.92 (1H, d, J 14.7 Hz), 3.81 (1H, br s), 3.69–3.64 (2H, m), 2.87 (1H, dd, J 7.0 Hz, 14 Hz), 2.55 (1H, dd, J 9.0 Hz 14.0 Hz), 2.20–2.11 (1H, m), 1.68–1.52 (3H, m), 1.41–1.19 (12H, m), 0.99–0.85 (9H, m), 0.80–0.72 (6H, m).

DESCRIPTION 19

(p-Toluenesulphonyloxy)propan-2-ol p-Toluenesulphonyl chloride (19.4 g, 102 mmol) was added to a stirred solution of propane-1,2-diol (30 ml), triethylamine (15 ml, 106 mmol), N,N-dimethylamine (108 mg, 0.87 mmol) in dichloromethane (100 ml) at +5° C. The mixture was stirred for 2 hours at +5° C. and overnight at room temperature then diluted with diethyl ether (300 ml) and washed 2M aqueous hydrochloric acid, water (twice) and brine. The combined organic extracts were dried (Na$_2$SO$_4$) and concentrated to give the title compound (22.8 g, 97%).

$\delta_H$ (360 MHz, CDCl$_3$): 7.80 (2H, m), 7.36 (2H, m), 4.08–3.96 (3H, m), 3.86 (1H, dd, J 7.0 Hz, 9.8 Hz), 2.45 (3H, s), 2.20 (1H, br), 1.16 (3H, d, J 6.3 Hz).

DESCRIPTION 20

2-(2-Iodo-4-trifluoromethoxyphenyloxy)-1-(p-toluenesulphonyloxy)propane

Diethyl azodicarboxylate (5 ml, 31.8 mmol) was added dropwise to a stirred solution of (p-toluenesulphonyloxy)propan-2-ol (Description 19; 7.6 g, 33 mmol), triphenylphosphine (9.0 g, 34 mmol) and 2-iodo-4-trifluoromethoxyphenol (10 ml, 33 mmol) at room temperature. The reaction mixture was stirred at room temperature for 2 hours and concentrated in vacuo. The residue was purified by chromatography on silica gel (iso-hexane:ethyl acetate) to give the title compound (18.7 g).

$\delta_H$ (400 MHz, CDCl$_3$): 7.77 (2H, dm, J 8.2 Hz), 7.60 (1H, d, J 3.1 Hz), 7.30 (2H, m), 7.13 (1H, ddt, J 0.8 Hz, J 3.1 Hz, 9.0 Hz), 6.75 (1H, d, J 9.2 Hz), 4.57 (1H, m), 4.21 (1H, dd, J 6.3 Hz, 10.6 Hz), 4.15 (1H, dd, J 4.3 Hz, 10.6 Hz), 2.43 (3H, s), 1.37 (3H, d, J 6.3 Hz).

DESCRIPTION 21

2,3-Dihydro-2-methyl-5-trifluoromethoxybenzofuran 10 ml solution of (2-iodo-4-trifluoromethoxyphenyloxy)-1-p-toluenesulphonyloxypropane (Description 20; 16 g, 28 mmol) in tetrahydrofuran (50 ml) was added dropwise to a stirred mixture of magnesium turnings (5 g, 208 mmol) in tetrahydrofuran (20 ml). 1,2-Dibromoethane (0.1 ml) was added. The exothermic reaction started. The mixture was warm up to reflux and the rest of (2-iodo-4-trifluoromethoxyphenyloxy)-1-p-toluenesulphonyloxypropane solution was added dropwise. The reaction mixture was heated at reflux for 24 hours, then cooled to room temperature and quenched with 2M aqueous hydrochloric acid. The mixture was extracted with a 1:1 mixture iso-hexane:diethyl ether (3×100 ml). The combined organic extracts were dried (Na$_2$SO$_4$) and concentrated. The residue was purified by chromatography on silica gel (iso-hexane:diethyl ether 0–15%) to give the title compound (2.8 g, 36%).

δ$_H$ (360 MHz, CDCl$_3$): 7.00 (1H, br s), 6.94 (1H, dm, J 8.4 Hz), 6.68 (1H, d, J 8.8 Hz), 4.97 (1H, m), 3.31 (1H, dd, J 8.8 Hz, 15.4 Hz), 2.82 (1H, dd, J 7.7 Hz, 15.8 Hz), 1.46 (3H, d, J 6.3 Hz).

DESCRIPTION 22

2,3-Dihydro-7-iodo-2-methyl-5-trifluoromethoxybenzofuran

Iodine (2.8 g, 11 mmol) was added in few portions to a stirred mixture of 2,3-dihydro-2-methyl-5-trifluoromethoxybenzofuran (Description 21; 2.8 g, 12.8 mmol), silver(I) trifluoroacetate (3.5 g, 15.8 mmol) in chloroform (60 ml). The mixture was stirred at room temperature for 1 hour, filtered through a pad of Celite™ and concentrated. The residue was treated with iso-hexane (150 ml), washed with aqueous sodium sulphite. The organic layer was dried (Na$_2$SO$_4$) and concentrated. The residue was purified by chromatography on silica gel (iso-hexane:diethyl ether 0–4%) to give the title compound (3.76 g, 85%).

δ$_H$ (400 MHz, CDCl$_3$): 7.00 (1H, dd, J 0.8 Hz, 1.6 Hz), 6.99 (1H, d, J 0.8 Hz), 5.05 (1H, m), 3.45 (1H, dd, J 9.0 Hz, 16.0 Hz), 2.94 (1H, dd, J 7.8 Hz, 16.0 Hz), 1.52 (3H, d, J 6.3 Hz).

DESCRIPTION 23

(1R*,5S*,6RS)-8-Benzyl-6-(tert-butoxycarbonyl)-1-phenyl-8-azabicyclo[3.2.1]oct-3-en-2-one A mixture of N-benzyl-3-hydroxy-2-phenylpyridinium bromide (255 g, 0.745 mol), tert-butyl acrylate (470 ml), triethylamine (150 ml) and 1,4-dioxane (1 l) was heated at reflux for 15 hours and cooled to room temperature. The reaction mixture was poured onto saturated aqueous NaHCO$_3$ (1 l) and extracted into an 1:1 mixture of iso-hexane:diethyl ether (3×500 ml). The combined organic extracts were dried (Na$_2$SO$_4$) and concentrated. The residue was purified by chromatography on silica gel (750 g, iso-hexane:diethyl ether 0–20%) to give a 2:1 mixture of (1R*,5S*,6R*)-8-benzyl-6-(tert-butoxycarbonyl)-1-phenyl-8-azabicyclo[3.2.1]oct-3-en-2-one and (1R*,5S*,6S*)-8-benzyl-6-(tert-butoxycarbonyl)-1-phenyl-8-azabicyclo[3.2.1]oct-3-en-2-one (205 g, 70%) as a yellow-orange foam. The isomers were separated on silica gel (iso-hexane:diethyl ether) and crystallised from iso-hexane:diethyl ether giving yellow rhombs:

DESCRIPTION 23a

(1R*,5S*,6R*)-8-Benzyl-6-(tert-butoxycarbonyl)-1-phenyl-8-azabicyclo[3.2.1]oct-3-en-2-one δ$_H$ (360 MHz, CDCl$_3$): 7.83 (1H, dd, J 1.4 Hz, 8.6 Hz), 7.40–7.25 (8H, m), 6.91 (1H, dd, J 4.8 Hz, 9.7 Hz), 6.18 (1H, d, J 9.7 Hz), 4.10 (1H, d, J 4.8 Hz), 3.67 (1H, d, J 13.0 Hz), 3.51 (1H, d, J 14.0 Hz), 2.99 (1H, dd, J 2.6 Hz, 14.2 Hz), 2.84 (1H, dd, J 2.6 Hz, 9.0 Hz), 2.39 (1H, dd, J 9.0 Hz, 14.2 Hz), 1.43 (9H, s).

DESCRIPTION 23b

(1R*,5S*,6S*)-8-Benzyl-6-(tert-butoxycarbonyl)-1-phenyl-8-azabicyclo[3.2.1]oct-3-en-2-one δ$_H$ (360 MHz, CDCl$_3$): 7.70 (1H, dd, J 1.3 Hz, 8.7 Hz), 7.40–7.25 (8H, m), 6.88 (1H, dd, J 4.8 Hz, 9.8 Hz), 6.25 (1H, d, J 9.8 Hz), 4.02 (1H, dd, J 5.0 Hz, 6.0 Hz), 3.65–3.50 (3H, m), 2.60 (2H, m), 1.43 (9H, s).

DESCRIPTION 24

(1R*,5S*,6RS)-8-Benzyl-6-(tert-butoxycarbonyl)-1-phenyl-8-azabicyclo[3.2.1]octan-2-one A mixture of (1R*,5S*,6RS)-8-benzyl-6-(tert-butoxycarbonyl)-1-phenyl-8-azabicylco[3.2.1]oct-3-en-2-one (Description 23; 26 g, 66 mmol), 10% palladium on charcoal (3.5 g, 3.3 mmol), ethyl acetate (50 ml) and methanol (100 ml) was stirred under hydrogen atmosphere (1 atm) at room temperature for 1 hour. The reaction mixture was treated with dichloromethane (500 ml), filtered through a pad of Celite™. The filter cake was well washed with dichloromethane and the filtrate was concentrated to give the title compound as a solid (26 g, 100%). The isomers were separated on silica gel (iso-hexane:ethyl acetate) and crystallised from acetone:iso-hexane yielding pure ketones as a colourless crystals.

6R*-epimer: δ$_H$ (360 MHz, CDCl$_3$): 7.50 (2H, dm, J 7.2 Hz), 7.41 (2H, d, J 7.3 Hz), 7.33 (4H, m), 7.25 (2H, m), 3.72 (1H, m), 3.70 (1H, d, J 15.0 Hz), 3.44 (1H, d, J 14.6 Hz), 2.91 (1H, dd, J 5.2 Hz, 9.5 Hz), 2.75–2.45 (5H, m), 1.97–1.87 (1H, m), 1.46 (9H, s).

6S*-epimer: δ$_H$ (360 MHz, CDCl$_3$): 7.50–7.20 (10H, m), 3.75 (1H, d, J 14.7 Hz), 3.61 (1H, dd, J 3.5 Hz, 6.3 Hz), 3.52 (1H, d, J 14.8 Hz), 3.46 (1H, dt, J 6.7 Hz, 11.6 Hz), 2.95 (1H, m), 2.90 (1H, dd, J 7.0 Hz, 14.4 Hz), 2.53–2.36 (2H, m), 2.26 (1H, dd, J 11.6 Hz, 14.0 Hz), 1.94 (1H, d, J 14.0 Hz), 1.91 (1H, m), 1.46 (9H, s).

DESCRIPTION 25

(1R*,2S*,5S*,6RS)-8-Benzyl-6-(tert-butoxycarbonyl)-2-(3-hydroxypropynyl)-1-phenyl-8-azabicyclo[3.2.1]octan-2-ol A solution of n-butyl lithium in hexanes (1.6M, 34 ml, 55.4 mmol) was added dropwise to a stirred solution of O-trimethylsilyl propargyl alcohol (8 ml, 52 mmol) in tetrahydrofuran (40 ml) at −78° C. This solution was added via syringe to a stirred solution of (1R*,5S*,6RS)-8-benzyl-6-(tert-butoxycarbonyl)-1-phenyl-8-azabicyclo[3.2.1]octan-2-one (Description 24; a 3:1 mixture of C6 epimers, 5 g, 12.7 mmol) in tetrahydrofuran (30 ml) at −78° C. over 30 minutes. The reaction mixture was stirred for 1 hour and quenched with acetic acid (3.1 ml), warm up to room temperature and concentrated in vacuo. The residue was treated with tetrahydrofuran (50 ml) followed by 1M solution of tetra-n-butylammonium fluoride in tetrahydrofuran (75 ml). The mixture was stirred for 30 minutes and concentrated in vacuo. The residue was treated with ethyl acetate (200 ml), washed with water and brine, dried (Na$_2$SO$_4$) and concentrated. The residue was purified by chromatography on silica gel (iso-hexane:ethyl acetate) to give the title compound (4.05 g, 71%) as a 3:1 mixture of C6 epimers.

6S*-epimer: δ$_H$ (400 MHz, CDCl$_3$): 7.51 (2H, m), 7.40–7.20 (8H, m), 4.31 (1H, s), 4.07 (1H, s), 3.95 (1H, d, J 14.8 Hz), 3.72 (1H, s), 3.05 (1H, d, J 14.9 Hz), 2.96 (1H, dd, J 5.5 Hz, 13.3 Hz), 2.87 (1H, dd, J 5.5 Hz, 9.4 Hz), 2.77 (1H, dd, J 9.4 Hz, 13.3 Hz), 2.10–1.90 (2H, m), 1.70–1.50 (1H, m), 1.44 (9H, s).

6R*-epimer: (distinguishable signals) δ$_H$ (400 MHz, CDCl$_3$): 7.44 (2H, m), 4.41 (1H, s), 4.09 (1H, d, J 14.8 Hz), 4.06 (1H, s), 3.56 (1H, dt, J 6.3 Hz, 12.5 Hz), 3.47 (1H, m), 3.06 (1H, d, J 14.8 Hz), 2.58 (1H, dd, J 12.1 Hz, 14.1 Hz), 1.46 (9H, s).

DESCRIPTION 26

(1R*,2S*,5S*,6RS)-8-Benzyl-6-(tert-butoxycarbonyl)-2-[(Z)-3-hydroxypropenyl]-1-phenyl-8-azabicyclo[3.2.1]octan-2-ol A mixture of (1R*,2S*,5S*,6RS)-8-benzyl-2-(3-hydroxypropynyl)-1-phenyl-6-(tert-butoxycarbonyl)-8- azabicyclo[3.2.1]octan-2-ol (Description 25; a 3:1 mixture of C6 epimers, 4 g, 8.9 mmol), Lindlar catalyst (800 mg) and ethyl acetate (30 ml) was stirred under hydrogen atmosphere (1 atm) at room temperature for 45 minutes. The reaction mixture was filtered through a pad of Celite™. The filtrate was concentrated to give the title compound (4.0 g, 100%) as a 3:1 mixture of C6 epimers.

6S*-epimer: $\delta_H$ (400 MHz, CDCl$_3$): 7.40–7.20 (10H, m), 5.42–5.30 (2H, m), 5.06 (1H, br), 3.91 (1H, d, J 14.5 Hz), 3.87–3.70 (2H, m), 3.67–3.57 (1H, m), 3.31 (1H, d, J 14.5 Hz), 2.98–2.86 (2H, m), 2.62 (1H, dd, J 8.6 Hz, 12.9 Hz), 2.35 (1H, br), 1.98 (1H, m), 1.79 (1H, m), 1.59 (2H, m), 1.44 (9H, s).

6R*-epimer: (distinguishable signals) $\delta_H$ (400 MHz, CDCl$_3$): 4.07 (1H, d, J 14.9 Hz), 3.48 (1H, m), 3.04 (1H, d, J 14.9 Hz), 2.54 (1H, dd, J 12.3 Hz, 13.7 Hz), 1.46 (9H, s).

DESCRIPTION 27

(1R*,2R*,5S*,6RS)-8-Benzyl-6-(tert-butoxycarbonyl)-1-phenylspiro[8-azabicyclo[3.2.1]octane-2,2'(5'H)-furan]

The mixture of (1R*,2S*,5S*,6RS)-8-benzyl-6-(tert-butoxycarbonyl)-2-[(Z)-3-hydroxypropenyl]-1-phenyl-8-azabicylco[3.2.1]octan-2-ol (Description 26; a 3:1 mixture of C6 epimers, 4.0 g, 8.9 mmol), diethyl azodicarboxylate (1.8 ml, 11.4 mmol), triphenylphosphine (3.6 g, 13.7 mmol), tetrahydrofuran (30 ml) was stirred at room temperature for 15 minutes. The mixture was treated with water (0.1 ml) and concentrated in vacuo. The residue was treated with diethyl ether followed by iso-hexane. The solid was filtered off and the filtrate was concentrated and purified by chromatography on silica gel (iso-hexane:diethyl ether 0–20%) to give the title compound (3.1 g, 81%) as a 3:1 mixture of C6 epimers.

6R*-epimer: $\delta_H$ (400 MHz, CDCl$_3$): 7.56 (2H, dm, J 7.2 Hz), 7.42 (2H, d, J 7.4 Hz), 7.27 (1H, t, J 7.2 Hz), 7.20–7.15 (5H, m), 5.57 (1H, dt, J 2.4 Hz, 6.3 Hz), 5.45 (1H, dt, J 1.6 Hz, 6.3 Hz), 4.51 (1H, dt, J 2.3 Hz, 12.5 Hz), 4.13 (1H, dt, J 2.0 Hz, 12.9 Hz), 3.81 (1H, d, J 14.9 Hz), 3.71 (1H, t, J 2.7 Hz), 3.00 (1H, d, J 14.8 Hz), 2.98–2.87 (2H, m), 2.40 (1H, dd, J 7.4 Hz, 11.8 Hz), 2.11 (1H, ddt, J 2.4 Hz, 5.5 Hz, 12.5 Hz), 1.80 (1H, dt, J 5.8 Hz, 14.5 Hz), 1.70 (1H, dd, J 5.4 Hz, 14.4 Hz), 1.62–1.51 (2H, m), 1.43 (9H, s).

6S*-epimer: $\delta_H$ (360 MHz, CDCl$_3$): 7.48 (4H, m), 7.32 (1H, t, J 7.1 Hz), 7.26–7.16 (5H, m), 5.60 (1H, dt, J 2.5 Hz, 6.3 Hz), 5.39 (1H, dt, J 1.8 Hz, 6.3 Hz), 4.48 (1H, dt, J 1.8 Hz, 13.0 Hz), 4.06 (1H, ddd, J 1.8 Hz, 2.5 Hz, 13.0 Hz), 3.97 (1H, d, J 14.7 Hz), 3.60–3.48 (4H, m), 2.96 (1H, d, J 14.7 Hz), 2.77 (1H, dd, J 4.9 Hz, 13.3 Hz), 2.56 (1H, dd, J 11.9 Hz, 13.3 Hz), 2.05 (1H, ddt, J 2.4 Hz, 4.9 Hz, 14.0 Hz) 2.00 (1H, dt, 5.3 Hz, 14.0 Hz), 1.69 (1H, m), 1.60–1.50 (1H, m), 1.45 (9H, s).

DESCRIPTION 28

(1R*,2R*,4'S*,5R*)-8-Benzyl-4'-(2-benzyloxy-5-trifluoromethoxyphenyl)-6-(tert-butoxycarbonyl)-2',3',4',5'-tetrahydro-1-phenylspiro[8-azabicyclo[3.2.1]octane-2,2'-furan]

A mixture of (1R*,2R*,5S*,6RS)-8-benzyl-6-(tert-butoxycarbonyl)-1-phenylspiro[8-azabicyclo[3.2.1]octane-2,2'(5'H)-furan] (Description 27; 3.1 g, 7.17 mmol), 2-benzyloxy-5-trifluoromethoxyphenyl iodide (8.7 g, 22.1 mmol), tetra-n-butylammonium chloride (2.0 g, 6.2 mmol), lithium chloride (3.45 g, 77.5 mmol), potassium formate (2.8 g, 33 mmol), palladium(II) acetate (250 mg, 1.1 mmol), water (0.5 ml) and N,N-dimethylformamide (30 ml) was stirred at +70° C. for 20 hours. An additional batch of 2-benzyloxy-5-trifluoromethoxyphenyl iodide (3.6 g, 9.1 mmol) and palladium(II) acetate (130 mg, 0.56 mmol) was added and the reaction mixture was stirred at +70° C. for 24 hours. The mixture was cooled to room temperature, quenched with water and extracted into a 1:1 mixture of iso-hexane:diethyl ether (3×100 ml). The combined organic extracts were dried (Na$_2$SO$_4$) and concentrated. The residue was purified by chromatography on silica gel. (iso-hexane:diethyl ether 0–45%) to give the title compound (3 g, 60%).

$\delta_H$ (360 MHz, CDCl$_3$): 7.53 (2H, dm, J 7.4 Hz), 7.48–7.05 (13H, m), 6.93 (1H, ddd, J 1.0 Hz, 2.8 Hz, 8.8 Hz), 6.76 (1H, d, J 2.8 Hz), 6.73 (1H, d, J 9.1 Hz), 4.88 (2H, s), 4.00 (1H, t, J 7.7 Hz), 3.75 (1H, d, J 14.7 Hz), 3.69 (1H, br s), 3.55 (1H, dd, J 8.1 Hz, 10.9 Hz), 2.99–2.83 (3H, m), 2.27 (1H, dd, J 8.8 Hz, 13.0 Hz), 2.18 (1H, dd, J 7.7 Hz, 12.3 Hz), 2.02 (1H, ddt, J 2.8 Hz, 5.3 Hz, 12.6 Hz), 1.80 (1H, dt, J 5.8 Hz, 14.5 Hz), 1.79 (1H, dd, J 5.3 Hz, 14.4 Hz), 1.60–1.46 (2H, m), 1.42 (9H, s).

EXAMPLE 1

(1R*,2R*,4'S*,5R*)-8-Benzyl-2',3',4',5'-tetrahydro-4'-[2-hydroxy-(5-trifluoromethoxy)phenyl]-1-phenylspiro[8-azabicyclo[3.2.1]octane-2,2'-furan]

Lithium naphthalenide (18 ml, 1.0M solution in tetrahydrofuran) was added dropwise to a −78° C. stirred solution of (1R*,2R*,4'S*,5S*,6R*)-8-benzyl-4'-(2-benzyloxy-5-trifluoromethoxyphenyl)-2',3',4',5'-tetrahydro-1-phenyl-6-phenylsulfonylspiro[8-azabicyclo[3.2.1]octane-2,2'-furan] (Description 16; 2 g, 2.7 mmol) in tetrahydrofuran (20 ml). After 15 minutes the mixture was quenched with saturated ammonium chloride then warmed to room temperature. The mixture was partitioned between ethyl acetate and brine. The organic layer was separated, dried (MgSO$_4$), filtered and concentrated. The residue was chromatographed on silica gel eluting with 5, 10 and 20% ethyl acetate/iso-hexanes to give the title compound (0.88 g, 64%).

$\delta_H$ (400MHz, CDCl$_3$): 7.67–7.65 (2H, m), 7.44 (2H, d, J 7.3 Hz), 7.40–7.08 (6H, m), 6.85 (1H, dd, J 2.0 Hz, 8.6 Hz), 6.72 (1H, d, J 2.6 Hz), 6.68 (1H, d, J 8.7 Hz), 3.91 (1H, t, J 7.3 Hz), 3.84 (1H, d, J 14.2 Hz), 3.61 (1H, dd, J 8.2 Hz, 10.6 Hz), 3.33 (1H, m), 2.83 (1H, d, J 14.3 Hz), 2.43 (td, 1H, 4.6 Hz), 2.27–2.00 (4H, m), 1.80–1.68 (3H, m), 1.45–1.39, (2H, m), 1.28–1.23 (1H, m).

EXAMPLE 2

(1R*,2R*,4'S*,5R*)-8-Benzyl-2',3',4',5'-tetrahydro-4'-(2-isopropoxy-5-trifluoromethoxyphenyl)-1-phenylspiro[8-azabicyclo[3.2.1]octane-2,2'-furan]

A mixture of (1R*,2R*,4'S*,5R*)-8-benzyl-2',3',4',5'-tetrahydro-4'-[2-hydroxy-(5-trifluoromethoxy)phenyl]-1-phenylspiro[8-azabicyclo[3.2.1]octane-2,2'-furan](Example 1; 150 mg, 0.29 mmol), 2-bromopropane (55 mg, 0.44 mmol) and potassium carbonate (100 mg, 0.73 mmol) were stirred at 50° C. in N,N-dimethylformamide, 5 ml for 18 hours. After this time the mixture was poured into brine, 50 ml and extracted with ethyl acetate (50 ml). The organic layer was washed (×3) with water then separated, dried (MgSO$_4$), filtered and concentrated in vacuo. The residue was chromatographed on silica gel eluting with 10% ethyl acetate/iso-hexanes to give the title compound. (87 mg, 54%).

$\delta_H$ (400 MHz, CDCl$_3$): 7.59–7.57 (2H, m), 7.38–7.36 (2H, m), 7.26–7.11 (6H, m), 6.85 (1H, dd, J 2.1 Hz, 8.8 Hz), 6.69 (1H, d, J 2.8 Hz), 6.58 (1H, d, J 8.9 Hz), 4.31 (1H, heptet, J 6.0 Hz), 3.95 (1H, t, J 7.5 Hz), 3.72 (1H, d, J 14.2 Hz), 3.44 (1H, dd, J 8.0 Hz, 10.8 Hz), 3.23 (1H, m), 2.77 (1H, d, J 14.2 Hz), 2.33 (1H, td, 4.6 Hz, 12.6 Hz), 2.24–1.97 (4H, m), 1.74–1.20 (6H, m), 1.14 (6H, m).

EXAMPLE 3

(1R*,2R*,4'S*,5R*)-8-Benzyl-4'-[2-(2,2-difluoroethoxy)-5-trifluoromethoxyphenyl]-2',3',4',5'-tetrahydro-1-phenylspiro[8-azabicyclo[3.2.1]octane-2,2'-furan]

Prepared in an analogous manner to Example 2 using 2-bromo-1,1-difluoroethane as an alkylating agent.

$\delta_H$ (400 MHz, CDCl$_3$): 7.66–7.64 (2H, m), 7.44–7.42 (2H, m), 7.34–7.18 (6H, m), 6.98 (1H, dd, J 2.9 Hz, 8.9 Hz), 6.81 (1H, d, J 2.8 Hz), 6.63 (1H, d, J 8.9 Hz), 6.14–5.82 (1H, tt, J 3.7 Hz, 54.6 Hz), 4.02–3.94 (3H, m), 3.80 (1H, d, J 14.2 Hz), 3.52 (1H, dd, J 8.0 Hz, 10.9 Hz), 3.33 (1H, m), 2.85 (1H, d, J 14.2 Hz), 2.41–2.04 (5H, m), 1.79–1.70 (4H, m), 1.50–1.43 (2H, m).

EXAMPLE 4

(1R*,2R*,4'S*,5R*)-8-Benzyl-2',3',4',5'-tetrahydro-1-phenyl-4'-[2-(2,2,2-trifluoroethoxy)-5-trifluoromethoxyphenyl]spiro[8-azabicyclo[3.2.1]octane-2,2'-furan]

Prepared in an analogous manner to Example 2 using 2,2,2-trifluoroethyltrichloromethanesulfonate as an alkylating agent.

$\delta_H$ (400 MHz, CDCl$_3$): 7.65–7.63 (2H, m), 7.44 (2H, m), 7.32–7.18 (6H, m), 6.96 (1H, m), 6.80 (1H, d, J 2.8 Hz), 6.64 (1H, d, J 8.9 Hz), 4.17–4.09 (2H, m), 4.02 (1H, t, J 7.5 Hz), 3.80 (1H, d, J 14.2 Hz), 3.52 (1H, dd, J 8.0 Hz, 10.8 Hz), 3.29 (1H, m), 2.82 (1H, d, 14.2 Hz), 2.43–2.00 (5H, m), 1.79–1.40 (6H, m).

EXAMPLE 5

(1R*,2R*,4'S*,5R*)-8-Benzyl-4'-[2-(2-fluoroethoxy)-5-trifluoromethoxyphenyl]-2',3',4',5'-tetrahydro-1-phenylspiro[8-azabicyclo[3.2.1]octane-2,2'-furan]

Prepared in an analogous manner Example 2 using 1-bromo-2-fluoroethane as an alkylating agent.

$\delta_H$ (400 MHz, CDCl$_3$): 7.59–7.58 (2H, m), 7.38–7.36 (2H, m), 7.33–7.11 (6H, m), 6.86 (1H, m), 6.71 (1H, d, J 2.7 Hz), 6.58 (1H, d, J 8.9 Hz), 4.67–4.65 (1H, m), 4.57–4.55 (1H, m), 4.07–3.90 (3H, m), 3.72 (1H, d, J 14.1 Hz), 3.51 (1H, dd, J 8.0 Hz, 10.9 Hz), 3.24 (1H, m), 2.77 (1H, d, J 14.2 Hz), 2.35 (1H, m), 2.21–1.91 (4H, m), 1.77–1.33 (6H, m).

EXAMPLE 6

(1R*,2R*,5S*,6R*)-8-Benzyl-2',5'-dihydro-4'-(2-methoxy-5-trifluoromethoxyphenyl)-1-phenyl-6-phenylsulfonylspiro[8-azabicyclo[3.2.1]octane-2,2'-furan]

Tetrakis(triphenylphosphine) palladium(0) (20 mg, 0,017 mmol) was added to a degassed suspension of (1R*,2R*,5S*,6R*)-8-Benzyl-2',5'-dihydro-1-phenyl-6-phenylsulfonyl-4'-tributylstannylspiro[8-azabicyclo[3.2.1]octane-2,2'-furan](Description 18; 150 mg, 0.2 mmol), lithium chloride (50 mg, 1.2 mmol), 2-methoxy-5-trifluoromethoxyiodobenzene (100 mg, 0.3 mmol) and copper(I) iodide (10 mg, 0.05 mmol) in toluene (10 ml). The mixture was heated to reflux for 18 hours. On cooling the mixture was diluted with ethyl acetate (50 ml) and filtered through Celite™. The filtrate was washed with water (25 ml) then dried (MgSO$_4$), filtered and concentrated in vacuo. The residue was chromatographed on silica gel eluting with 10, 20 and 30% ethyl acetate/iso-hexanes to give the title compound (115 mg, 87%).

$\delta_H$ (400 MHz, CDCl$_3$): 7.85–7.83 (2H, m), 7.63–7.59 (3H, m), 7.54–7.49 (4H, m), 7.37–7.33 (2H, m), 7.27–7.04 (5H, m), 6.80 (1H, d, J 9.0 Hz), 6.72 (1H, d, J 2.7 Hz), 6.20 (1H, t, J 2.0 Hz), 4.97 (1H, dd, J 2.1 Hz, 12.4 Hz), 4.60 (1H, dd, J 2.0 Hz, 12.4 Hz), 4.00 (1H, d, J 14.7 Hz), 3.85 (1H, s), 3.78 (3H, s), 3.71–3.65 (2H, m), 2.86 (1H, dd J 6.7 Hz, 14.0 Hz), 2.60 (1H, dd, J 9.2 Hz, 14.0 Hz), 2.21 (1H, m), 1.83–1.65 (3H, m).

EXAMPLE 7

(1R*,2R*,4'S*,5R*)-8-Benzyl-2',3',4',5'-tetrahydro-4'-[(2RS)-2,3-dihydro-2-methyl-5-trifluoromethoxybenzofuran-7-yl]-1-phenyl-6-phenylsulphonylspiro[8-azabicyclo[3.2.1]octane-2,2'-furan]

A mixture of (1R*,2R*,5S*,6R*)-8-benzyl-1-phenyl-6-phenylsulphonylspiro[8-azabicyclo[3.2.1]octane-2,2'(5'H)-furan] (Description 15; 500 mg, 1.05 mmol), 2,3-dihydro-7-iodo-2-methyl-5-trifluoromethoxybenzofuran (Description 22; 1.11 g, 3.22 mmol), tetra-n-butylammonium chloride (310 mg, 0.96 mmol), lithium chloride (640 mg, 1.48 mmol), potassium formate (420 mg, 5 mmol), palladium(II) acetate (47 mg, 0.21 mmol), water (0.2 ml) and N,N-dimethylformamide (5 ml) was stirred at +65° C. for 24 hours. An additional batch of 2,3-dihydro-7-iodo-2-methyl-5-trifluoromethoxybenzofuran (0.7 g, 2.0 mmol) and palladium(II) acetate (22 mg, 0.1 mmol) was added and the reaction mixture was stirred at +65° C. for 48 hours. The mixture was cooled to room temperature, quenched with saturated aqueous NaHCO$_3$ and extracted into diethyl ether. The combined organic extracts were dried (Na$_2$SO$_4$) and concentrated. The residue was purified by chromatography on silica gel (iso-hexane:diethyl ether 0–45%) to give the title compound (320 mg, 44%) as a 1:1 mixture of epimers.

$\delta_H$ (400 MHz, CDCl$_3$): 7.89 (2H, dm, J 7.4 Hz), 7.65–7.50 (8H, m), 7.33 (4H, m), 6.78 (1H, s), 6.415 (0.5H, d, J 1.6 Hz), 6.410 (0.5H, d, J 1.6 Hz), 4.81 (1H, m), 3.92 (1H, d, J 7.8 Hz), 3.88 (2H, d, J 9.4 Hz), 3.74 (1H, s), 3.71 (1H, d, J 7.8 Hz), 3.70 (0.5H, m), 3.66 (0.5H, dd, J 8.2 Hz, 11.0 Hz), 3.21 (0.5H, dd, J 3.1 Hz, 8.6 Hz), 3.16 (0.5H, dd, J 3.5 Hz, 11.0 Hz), 2.97 (1H, dd, J 7.8 Hz, 13.7 Hz), 2.68 (1H, dd, J 7.4 Hz, 15.6 Hz), 2.43 (1H, dd, J 9.0 Hz, 13.7 Hz), 2.12–1.97 (4H, m), 1.65–1.55 (2H, m), 1.49 (1H, m), 1.35 (1.5H, d, J 5.9 Hz), 1.34 (1.5H, d, J 6.3 Hz).

EXAMPLE 8

(1R*,2R*,4'S*,5R*)-6-(tert-Butoxycarbonyl)-2',3',4',5'-tetrahydro-4'-(2-hydroxy-5-trifluoromethoxyphenyl)-1-phenylspiro[8-azabicyclo[3.2.1]octane-2,2'-furan]

A mixture of (1R*,2R*,4'S*,5R*)-8-benzyl-4'-(2-benzyloxy-5-trifluoromethoxyphenyl)-6-(tert-butoxycarbonyl)-2',3',4',5'-tetrahydro-1-phenylspiro[8-azabicyclo[3.2.1]octane-2,2'-furan] (Description 28; 1.065 g, 1.52 mmol), 10% palladium on charcoal (340 mg, 0.32 mmol) and ethanol (20 ml) was stirred under hydrogen atmosphere (1 atm) at +65° C. for 1.5 hour. The reaction mixture was cooled to room temperature, flushed with nitrogen gas and filtered through a pad of Celite™. The filtrate was concentrated to give the title compound (900 mg, 97%).

$\delta_H$ (400 MHz, CDCl$_3$): 7.53 (2H, m), 7.40–7.30 (3H, m), 6.86 (1H, ddd, J 0.8 Hz, 3.1 Hz, 9.0 Hz), 6.73 (1H, d, J 2.7 Hz), 6.64 (1H, d, J 9.0 Hz), 3.79 (1H, t, J 7.4 Hz), 3.77 (1H, br s), 3.61 (1H, dd, J 8.2 Hz, 9.8 Hz), 2.87 (1H, dd, J 5.1 Hz, 8.6 Hz), 2.43 (1H, dd, J 8.6 Hz, 13.7 Hz), 2.39–2.31 (2H, m), 2.10 (1H, ddt, J 3.1 Hz, 5.9 Hz, 12.5 Hz), 1.83 (1H, dd, J 5.5 Hz, 14.5 Hz), 1.74 (1H, dd, J 5.5 Hz, 12.8 Hz), 1.69–1.56 (2H, m), 1.41 (9H, s).

EXAMPLE 9

(1R*,2R*,4'S*,5S*)-2',3',4',5'-Tetrahydro-4'-(2-methoxy-5-trifluoromethoxyphenyl)-1-phenylspiro[8-azabicyclo[3.2.1]octane-2,2'-furan]

A solution of lithium aluminium hydride in tetrahydrofuran (1M, 2 ml) was added to a stirred suspension of (1R*,2R*,4'S*,5S*,6R*)-2',3',4',5'-tetrahydro-4'-(2-methoxy-5-trifluoromethoxyphenyl)-1-phenyl-6-phenylsulphonylspiro[8-azabicyclo[3.2.1]octane-2,2'-furan]-5-one (Description 12; 100 mg, 0.17 mmol) in tetrahydrofuran (4 ml) at +5° C. The cold bath was removed and the reaction mixture was stirred at room temperature for 30 minutes. The mixture was diluted with dichloromethane and treated with small amount of saturated aqueous Na$_2$SO$_4$, stirred for 1 hour and filtered through a pad of Celite™. The filtrate was concentrated in vacuo. The residue was treated with tetrahydrofuran (3 ml) followed by triphenylphosphine (220 mg, 0.84 mmol) and diethyl azodicarboxylate (0.1 ml, 0.64 mmol) and stirred at room temperature overnight. The mixture was purified by chromatography on silica gel (dichloromethane:methanol) to give the title compound (35 mg, 48%).

$\delta_H$ (400 MHz, CDCl$_3$): 7.60–7.41 (3H, m), 7.33–7.25 (2H, m), 6.93 (1H, dd, J 2.0 Hz, 8.8 Hz), 6.74 (1H, d, J 2.5 Hz), 6.67 (1H, d, J 8.9 Hz), 5.70 (1H, br), 3.96 (1H, br s), 3.86 (1H, t, J 7.7 Hz), 3.64 (3H, s), 3.57 (1H, dd, J 8.0 Hz, 10.6 Hz), 2.99 (1H, d, J 8.6 Hz), 2.40–2.20 (3H, m), 1.92–1.75 (4H, m), 1.65 (1H, m), 1.50 (1H, m).

The hydrochloride salt of the title compound was prepared by treatment with ethereal HCl and recrystallisation from dichloromethane:iso-hexane.

HCl salt: $\delta_H$ (400 MHz, CDCl$_3$): 10.73 (1H, d, J 4.8 Hz), 8.96 (1H, d, J 4.8 Hz), 7.53 (2H, m), 7.38 (3H, m), 6.97 (1H, dd, J 2.0 Hz, 8.8 Hz), 6.70 (1H, d, J 2.5 Hz), 6.67 (1H, d, J 8.9 Hz), 4.90 (1H, br s), 3.94 (1H, t, J 7.9 Hz), 3.64 (3H, s), 3.61 (1H, dd, J 8.4 Hz, 10.8 Hz), 2.74 (1H, m), 2.64 (1H, dt, J 3.6 Hz, 12.7 Hz), 2.51 (1H, m), 2.40–2.25 (2H, m), 1.93–1.77 (4H, m), 1.70–1.55 (2H, m). MS (ES$^+$) 434 (M+H)$^+$.

EXAMPLE 10

(1R*,2R*,4'S*,5S*,6R*)-2',3',4',5'-Tetrahydro-4'-(2-hydroxy-5-trifluoromethoxyphenyl)-1-phenyl-6-phenylsulphonylspiro[8-azabicyclo[3.2.1]octane-2,2'-furan]

A mixture of (1R*,2R*,4'S*,5S*,6R*)-8-benzyl-2',3',4',5'-tetrahydro-4'-(2-benzyloxy-5-trifluoromethoxyphenyl)-1-phenyl-6-phenylsulphonylspiro[8-azabicyclo[3.2.1]octane-2,2'-furan](Description 16; 2.2 g, 2.97 mmol), 5% palladium on charcoal (3 g, 1.4 mmol) and ethanol (55 ml) was stirred under hydrogen atmosphere (1 atm) at +70° C. for 70 minutes. The reaction mixture was cooled to room temperature, flushed with nitrogen gas and filtered through a pad of Celite™. The filtrate was concentrated to give the title compound (1.77 g, quant.).

$\delta_H$ (400 MHz, CDCl$_3$): 7.90 (2H, dm, J 7.1 Hz), 7.68 (1H, m), 7.58 (2H, t, J 7.8 Hz), 7.52 (2H, dd, J 1.9 Hz, 7.9 Hz), 7.40–7.30 (3H, m), 6.86 (1H, dd, J 1.9 Hz, 8.9 Hz), 6.70 (1H, d, J 2.4 Hz), 6.65 (1H, d, J 8.7 Hz), 4.04 (1H, s), 3.83 (1H, t, J 7.7 Hz), 3.70–3.55 (2H, m), 2.57 (1H, dd, J 5.3 Hz, 14.4 Hz), 2.53 (1H, dd, J 8.6 Hz, 14.4 Hz), 2.34 (1H, dd, J 7.6 Hz, 12.7 Hz), 2.11 (1H, m), 1.85 (1H, dd, J 5.2 Hz, 14.6 Hz), 1.72 (1H, m), 1.58 (1H, dd, J 5.7 Hz, 14.1 Hz), 1.47 (1H, t, J 12.7 Hz), 1.46 (1H, m).

EXAMPLE 11

(1R*,2R*,4'S*,5S*,6R*)-2',3',4',5'-Tetrahydro-4'-(2-methoxy-5-trifluoromethoxyphenyl)-1-phenyl-6-phenylsulphonylspiro[8-azabicyclo[3.2.1]octane-2,2'-furan]

The mixture of (1R*,2R*,4S*,5S*,6R*)-2',3',4',5'-tetrahydro-4'-(2-hydroxy-5-trifluoromethoxyphenyl)-1-phenyl-6-phenylsulphonylspiro[8-azabicyclo[3.2.1]octane-2,2'-furan] (Example 10; 60 mg, 0.11 mmol), diethyl azodicarboxylate (0.04 ml, 0.25 mmol), triphenylphosphine (68 mg, 0.26 mmol), methanol (0.2 ml) and tetrahydrofuran (2 ml) was stirred at room temperature overnight then concentrated in vacuo and treated with methanol (2 ml) followed by 4M aqueous Na $\delta_H$ (0.4 ml). The mixture was stirred at room temperature for 24 hours, diluted with brine and extracted into dichloromethane. The combined organic extracts were dried (Na$_2$SO$_4$) and concentrated. The residue was purified by chromatography on silica gel (iso-hexane:ethyl acetate) to give the title compound (52 mg, 84%).

$\delta_H$ (400 MHz, CDCl$_3$): 7.90 (2H, dm, J 7.1 Hz), 7.66 (1H, m), 7.57 (2H, t, J 7.9 Hz), 7.90 (2H, dd, J 1.9 Hz, 8.1 Hz), 7.40–7.30 (3H, m), 6.94 (1H, dd, J 2.9 Hz, 9.0 Hz), 6.74 (1H, d, J 2.8 Hz), 6.66 (1H, d, J 8.9 Hz), 4.04 (1H, t, J 2.8 Hz), 3.80 (1H, t, J 7.6 Hz), 3.64 (1H, m), 3.64 (3H, s), 3.55 (1H, dd, J 8.2 Hz, 10.6 Hz), 2.56 (1H, dd, J 9.0 Hz, 14.5 Hz), 2.51 (1H, dd, J 8.6 Hz, 14.5 Hz), 2.30 (1H, dd, J 7.8 Hz, 12.9 Hz), 2.12 (1H, ddt, J 3.2 Hz, 5.5 Hz, 12.9 Hz), 1.92 (1H, tt, J 7.4 Hz, 11.0 Hz), 1.82 (1H, dd, J 5.1 Hz, 14.5 Hz), 1.54 (1H, dt, J 5.8 Hz, 13.7 Hz), 1.43 (1H, m), 1.38 (1H, dd, J 11.7 Hz, 12.5 Hz).

The hydrochloride salt of the title compound was prepared by treatment with ethereal HCl and recrystallisation from ethyl acetate:diethyl ether.

HCl salt: $\delta_H$ (400 MHz, MeOHd-d$_4$): 8.02 (2H, dm, J 8.6 Hz), 7.83 (1H, m), 7.72 (2H, t, J 8.0 Hz), 7.60–7.50 (5H, m), 7.03 (1H, dd, J 2.8 Hz, 9.0 Hz), 6.85 (1H, d, J 9.0 Hz), 6.82 (1H, d, J 2.8 Hz), 4.49 (1H, s), 4.38 (1H, dd, J 5.5 Hz, 9.4 Hz), 3.91 (1H, t, J 7.7 Hz), 3.67 (1H, m), 3.67 (3H, s), 3.03 (1H, dd, J 9.5 Hz, 15.0 Hz), 2.81 (1H, dd, J 5.4 Hz, 15.0 Hz), 2.34 (2H, dd, J 7.8 Hz, 13.0 Hz), 2.05–1.95 (2H, m), 1.95–1.75 (2H, m), 1.67 (1H, t, J 13.2 Hz). MS (ES$^+$) 574 (M+H)$^+$.

EXAMPLE 12

(1R*,2R*,4'S*,5S*)-4'-(2-Cyclopropyloxy-5-trifluoromethoxyphenyl)-2',3',4',5'-tetrahydro-1-phenylspiro[8-azabicyclo[3.2.1]octane-2,2'-furan]

Oxone (400 mg, 0.65 mmol) was added to a stirred mixture of (1R*,2R*,4'S*,5S*,6R*)-2',3',4',5'-tetrahydro-4'-

[2-(1-phenylthiocyclopropyloxy)-5-trifluoromethoxyphenyl]-1-phenyl-6-phenylsulphonylspiro[8-azabicyclo[3.2.1]octane-2,2'-furan] (Description 17; 88 mg, 0.12 mmol), wet aluminium oxide (5 g of $Al_2O_3$ in 1 ml of water, 370 mg) and chloroform (5 ml) at room temperature. The reaction mixture was stirred for 5 hours then filtered and concentrated to give crude disulphone (95 mg). Sodium amalgam (10%, 700 mg) was added in small portions to the stirred mixture of the disulphone (95 mg), disodium hydrogen orthophosphate (700 mg), and methanol (5 ml) at +5° C. After reaction went to completion, the mixture was quenched with saturated aqueous $NaHCO_3$, decanted and extracted into dichloromethane. The combined organic extracts were dried ($Na_2SO_4$) and concentrated. The residue was purified by chromatography on silica gel (dichloromethane:methanol) to give the title compound (34 mg, 60%).

$\delta_H$ (400 MHz, $CDCl_3$): 7.50–7.20 (5H, m), 7.04 (1H, d, J 8.9 Hz), 6.96 (1H, dt, J 2.0 Hz, 8.9 Hz), 6.72 ((H, d, J 2.5 Hz), 3.88 (1H, br s), 3.83 (1H, t, J 7.8 Hz), 3.56 (1H, m), 3.50 (1H, dd, J 8.0 Hz, 10.6 Hz), 2.40–2.10 (4H, m), 1.90–1.70 (5H, m), 1.57 (5H, m), 1.50 (4H, t, J 11.7 Hz), 0.74 (2H, m), 0.62 (2H, m).

The hydrochloride salt of the title compound was prepared by treatment with ethereal HCl and recrystallisation from ethyl acetate:iso-hexane.

HCl salt: $\delta_H$ (360 MHz, $CDCl_3$): 7.51 (5H, m), 7.20 (1H, d, J 9.0 Hz), 7.05 (1H, ddd, J 0.9 Hz, 2.8 Hz, 9.0 Hz), 6.85 (1H, d, J 2.8 Hz), 4.07 (1H, dd, J 3.1 Hz, 7.0 Hz), 3.90 (1H, t, J 7.4 Hz), 3.67 (1H, m), 3.60 (1H, dd, J 8.1 Hz, 10. 6 Hz), 2.63 (1H, ddd, J 5.0 Hz, 10.6 Hz, 14.4 Hz), 2.50–2.20 (7H, m), 1.95–1.77 (2H, m), 1.76 (1H, t, J 11.7 Hz), 0.79 (2H, m), 0.60 (1H, m), 0.53 (1H, m). MS (ES$^+$) 460 (M+H)$^+$.

EXAMPLE 13

(1R*,2R*,4'S*,5R*)-2',3',4',5'-Tetrahydro-4'-(2-isopropoxy-5-trifluoromethoxyphenyl)-1-phenylspiro[8-azabicyclo[3.2.1]octane-2,2'-furan] hydrochloride Palladium hydroxide, 20 mg was added to a solution of (1R*,2R*,4'S*,5R*)-8-benzyl-2',3',4',5'-tetrahydro-4'-(2-isopropoxy-5-trifluoromethoxyphenyl)-1-phenylspiro[8-azabicyclo[3.2.1]octane-2,2'-furan] (Example 2; 84 mg, 0.15 mmol) in ethanol (3 ml). The mixture was hydrogenated at 45 psi. using the Parr® apparatus for 4 hours. The mixture was filtered through Celite™ and the filtrate concentrated in vacuo. The residue was chromatographed on silica gel eluting with 150:8:1, dichloromethane:methanol:ammonia to give the title compound (42 mg, 60%).

The hydrochloride salt was prepared by treatment with ethereal HCl.

$\delta_H$ (400 MHz, MeOH-$d_4$): 7.50 (5H, br s), 7.02 (1H, dd, J 2.0 Hz, 9.0 Hz), 6.87–6.85 (2H, m), 4.48 (1H, heptet, J 6.0 Hz), 4.06 (1H, m), 3.98 (1H, t, J 7.7 Hz), 3.57 (1H, dd, J 8.0 Hz, 10.8 Hz), 2.63 (1H, m), 2.46–1.78 (10H, m), 1.2 (3H, d, J 6.0 Hz), 1.17 (3H, d, J 6.0 Hz). MS (ES)$^+$ 462 (M+H)$^+$.

EXAMPLE 14

(1R*,2R*,4'S*,5R*)-2',3',4',5'-Tetrahydro-4'-(2-(2',2'-difluoro)ethoxy-5-trifluoromethoxyphenyl)-1-phenylspiro[8-azabicyclo[3.2.1]octane-2,2'-furan] hydrochloride Prepared in an analogous manner to Example 13 from Example 3.

$\delta_H$ (360 MHz, MeOH-$d_4$): 7.51 (5H, br s), 7.08 (1H, dd, J 1.8 Hz, 8.1 Hz), 6.92 (1H, d, J 9.0 Hz), 6.87 (1H, d, J 2.7 Hz), 6.25–5.94 (1H, tt, J 3.6 Hz, 54.7 Hz), 4.16–3.96 (4H, m), 3.68–3.63 (1H, m), 2.65–2.60 (1H, m), 2.46–1.79 (10H, m). MS (ES)$^+$ 484 (M+H)$^+$.

EXAMPLE 15

(1R*,2R*,4'S*,5R*)-2',3',4',5'-Tetrahydro-1-phenyl-4'-[2-(2,2,2-trifluoroethoxy)-5-trifluoromethoxyphenyl)spiro[8-azabicyclo[3.2.1]octane-2,2'-furan]hydrochloride Prepared in an analogous manner to Example 13 from Example 4.

$\delta_H$ (400 MHz, MeOH-$d_4$): 7.50 (5H, br s), 7.09 (1H, dd, J 1.9 Hz, 8.6 Hz), 6.94 (1H, d, J 8.9 Hz), 6.90 (1H, d, J 2.4 Hz), 4.47–4.40 (2H, m), 4.08–4.00 (2H, m), 3.64 (1H, t, J 8.4 Hz), 2.66 (1H, m), 2.47–1.79 (10H, m). MS (ES)$^+$ 502 (M+H)$^+$.

EXAMPLE 16

(1R*,2R*,4'S*,5R*)-4'-[2-(2-Fluoroethoxy)-5-trifluoromethoxyphenyl]-2',3',4',5'-tetrahydro-1-phenylspiro[8-azabicyclo[3.2.1]octane-2,2'-furan] hydrochloride Prepared in an analogous manner to Example 13 from Example 5.

$\delta_H$ (400 MHz, MeOH-$d_4$): 7.51 (5H, br s), 7.05 (1H, dd, J 1.9 Hz, 9.0 Hz), 6.88 (1H, d, J 9.0 Hz), 6.82 (1H, d, J 2.7 Hz), 4.73 (1H, m), 4.61 (1H, m), 4.11 (1H, m), 4.07–4.04 (2H, m), 4.00 (1H, t, J 7.5 Hz), 3.69 (1H, dd, J 8.0 Hz, 10.7 Hz), 2.64–2.59 (1H, m), 2.46–2.39 (2H, m), 2.31–2.04 (4H, m), 1.94–1.79 (4H, m). MS (ES)$^+$ 466 (M+H)$^+$.

EXAMPLE 17

(1R*,2R*,4'R*,5S*,6R*)-2',3',4',5'-Tetrahydro-4'-(2-methoxy-5-trifluoromethoxyphenyl)-1-phenyl-6-phenylsulphonylspiro[8-azabicyclo[3.2.1]octane-2,2'-furan]hydrochloride 10% Palladium on carbon (100 mg) was added as a slurry in water (1 ml) to a solution of (1R*,2R*,5S*,6R*)-8-benzyl-2',5'-dihydroxy-4'-(2-methoxy-5-trifluoromethoxyphenyl)-1-phenyl-6-phenylsulfonylspiro[8-azabicyclo[3.2.1]octane-2,2'-furan] (Example 6; 113 mg, 0.17 mmol) in methanol (10 ml). The mixture was hydrogenated using the Parr® apparatus at 50 psi. for 20 hours. The mixture was filtered through Celite™ and the filtrate concentrated in vacuo. The residue was chromatographed on silica gel eluting with 180:8:1, dichloromethane:methanol:ammonia to yield the title compound (83 mg, 86%). The hydrochloride salt was prepared by treatment with ethereal HCl.

$\delta_H$ (400 MHz, MeOH-$d_4$): 8.03–8.01 (2H, m), 7.85–7.83 (1H, m), 7.83–7.81 (2H, m), 7.56–7.34 (5H, m), 7.00 (1H, m), 6.88 (1H, d, J 9.0 Hz), 6.12 (1H, t, 2.2 Hz), 4.54 (1H, s), 4.43 (1H, m), 4.11 (1H, m), 3.93–3.85 (1H, m), 3.69 (3H, m), 3.06–2.97 (2H, m), 2.83–2.78 (1H, m), 2.40–2.34 (1H, m), 2.13–1.81 (5H, m). MS(ES)$^+$ 574 (M+H)$^+$.

EXAMPLE 18

(1R*,2R*,4'S*,5R*)-2',3',4',5'-Tetrahydro-4'-[(2RS)-2,3-dihydro-2-methyl-5-trifluoromethoxybenzofuran-7-yl]-1-phenyl-6-phenylsulphonylspiro[8-azabicyclo[3.2.1]octane-2,2'-furan]

A mixture of (1R*,2R*,4S*,5R*)-8-benzyl-2',3',4',5'-tetrahydro-4'-[(2RS)-2,3-dihydro-2-methyl-5- trifluoromethoxybenzofuran-7-yl]-1-phenyl-6-phenylsulphonylspiro[8-azabicyclo[3.2.1]octane-2,2'-furan] (Example 7; 200 mg, 0.29 mmol), 10% palladium on charcoal (375 mg, 0.35 mmol) and ethanol (25 ml) was stirred under hydrogen atmosphere (1 atm) at +70° C. for 30 minutes. The reaction mixture was cooled to room temperature, flushed with nitrogen gas and filtered through a pad of Celite™. The filtrate was concentrated to give the title compound (160 mg, 92%).

$\delta_H$ (360 MHz, MeOH-$d_4$): 8.02 (2H, dm, J 8.1 Hz), 7.82 (1H, t, J 7.3 Hz), 7.72 (2H, t, J 7.8 Hz), 7.33 (5H, m), 6.89 (1H, s), 6.44 (1H, br s), 4.84 (1H, m), 4.44 (1H, s), 4.37 (1H, dd, J 5.3 Hz, 9.1 Hz), 3.87 (1H, dt, J 8.1 Hz, 13.7 Hz), 3.73 (1H, q, J 9.8 Hz), 3.23 (1H, dd, J 8.8 Hz, 16.1 Hz), 2.99 (1H, dd, J 9.5 Hz, 15.1 Hz), 2.77 (1H, dd, J 5.3 Hz, 15.0 Hz), 2.71 (1H, dd, J 7.7 Hz, 16.1 Hz), 2.28 (2H, m), 1.96 (2H, m), 1.80 (2H, m), 1.56 (1H, m), 1.35 (3H, d, J 6.3 Hz).

EXAMPLE 19

(1R*,2R*,4'S*,5S*)-2',3',4',5'-Tetrahydro-4'-((2RS)-2,3-dihydro-2-methyl-5-trifluoromethoxybenzofuran-7-yl]-1-phenylspiro[8-azabicyclo[3.2.1]octane-2,2'-furan]

Sodium amalgam (10%, 2 g) was added in small portions to stirred mixture of (1R*,2R*,4S*,5R*)-2',3',4',5'-tetrahydro-4'-[(2RS)-2,3-dihydro-2-methyl-5-trifluoromethoxybenzofuran-7-yl]-1-phenyl-6-phenylsulphonylspiro[8-azabicyclo[3.2.1]octane-2,2'-furan] (Example 18; 160 mg, 0.26 mmol), disodium hydrogen orthophosphate (500 mg), methanol (10 ml) at +5° C. After reaction went to completion, the mixture was quenched with saturated aqueous NaHCO$_3$, decanted and extracted into dichloromethane. The combined organic extracts were dried (Na$_2$SO$_4$) and concentrated. The residue was purified by chromatography on silica gel (dichloromethane:methanol) to give the title compound (83 mg, 67%).

$\delta_H$ (400 MHz, CDCl$_3$): 7.40–7.20 (5H, m), 6.79 (1H, s), 6.45 (0.5H, d, J 1.6 Hz), 6.43 (0.5H, d, J 1.6 Hz), 4.88 (1H, m), 3.76 (1H, m), 3.70–3.55 (2H, m), 3.21 (0.5H, dd, J 5.0 Hz, 15.0 Hz), 3.19 (0.5H, dd, J 4.9 Hz, 15.0 Hz), 2.69 (1H, dd, J 7.4 Hz, 15.7 Hz), 2.27 (1H, m), 2.15 (3H, m), 2.01 (1H, ddt, J 2.7 Hz, 5.9 Hz, 12.5 Hz), 1.87 (1H, ddt, J 2.7 Hz, 5.1 Hz, 14.1 Hz), 1.81–1.48 (5H, m), 1.38 (1.5H, d, J 6.3 Hz), 1.37 (1.5H, d, J 6.3 Hz).

The hydrochloride salt of the title compound was prepared by treatment with ethereal HCl and recrystallisation from dichloromethane: tert-butyl methyl ether.

HCl salt: $\delta_H$ (360 MHz, -$d_4$): 7.51 (5H, m), 6.90 (1H, s), 6.48 (0.5H, s), 6.47 (0.5H, s), 4.88 (1H, m), 4.07 (1H, m), 3.89 (0.5H, dd, J 5.3 Hz, 7.9 Hz), 3.87 (0.5H, dd, J 5.5 Hz, 7.6 Hz), 3.76 (0.5H, dd, J 8.2 Hz, 9.7 Hz), 3.73 (0.5H, dd, J 8.1 Hz, 9.7 Hz), 3.25 (1H, dd, J 8.7 Hz, 15.8 Hz), 2.73 (1H, dd, J 7.4 Hz, 15.8 Hz), 2.65 (0.5H, dd, J 4.7 Hz, 10.3 Hz), 2.62 (0.5H, dd, J 4.5 Hz, 9.7 Hz), 2.44 (1H, dd, J 4.2 Hz, 12.3 Hz), 2.40–20 (4H, m), 2.16 (1H, dd, J 4.0 Hz, 9.7 Hz), 2.13 (1H, dd, J 4.7 Hz, 9.2 Hz), 2.06 (1H, dd, J 5.5 Hz, 13.4 Hz), 1.97–1.75 (4H, m), 1.61 (1H, m), 1.36 (3H, d, J 6.3 Hz). MS (ES$^+$) 460 (M+H)$^+$.

EXAMPLE 20

(1R*,2R*,4'S*,5R*)-2',3',4',5'-Tetrahydro-4'-(2-methoxy-5-trifluoromethoxyphenyl)-6-(morpholin-1-ylcarbonyl)-1-phenylspiro[8-azabicyclo[3.2.1]octane-2,2'-furan]

Step (a)—The mixture of (1R*,2R*,4S*,5R*)-6-(tert-Butoxycarbonyl)-2',3',4',5'-tetrahydro-4'-(2-hydroxy-5-trifluoromethoxyphenyl)-1-phenylspiro[8-azabicyclo[3.2.1]octane-2,2'-furan] (Example 8; 900 mg, 1.73 mmol), diethyl azodicarboxylate (0.37 ml, 1.72 mmol), triphenylphosphine (800 mg, 3.0 mmol), methanol (1 ml) and tetrahydrofuran (10 ml) was stirred at room temperature for 2 hours. A few drops of water were added and the mixture was concentrated. The residue was purified by chromatography on silica gel to give a 1:1 mixture of (1R*,2R*,4S*,5R*)-6-(tert-butoxycarbonyl)-2',3',4',5'-tetrahydro-4'-(2-methoxy-5-trifluoromethoxyphenyl)-1-phenylspiro[8-azabicyclo[3.2.1]octane-2,2'-furan] and (1R*,2R*,4'S*,5R*)-6-(tert-butoxycarbonyl)-2',3',4',5'-tetrahydro-4'-(2-methoxy-5-trifluoromethoxyphenyl)-8-methyl-1-phenylspiro[8-azabicyclo[3.2.1]octane-2,2'-furan] 500 mg). This mixture was treated with dichloromethane (7 ml) and trifluoroacetic acid (3 ml) and stirred at room temperature for 24 hours and concentrated. The residue was treated with dichloromethane (6 ml) to form a solution of carboxylic acid.

Step (b)—A portion of the solution (2 ml) was treated with morpholine (0.15 ml, 1.72 mmol), triethylamine (0.2 ml, 2.7 mmol), 1-(3-dimethylaminopropyl)-3-ethylcarbodiimide hydrochloride (140 mg, 0.73 mmol), and 4-N,N-dimethylaminopyridine (10 mg, 0.08 mmol). The mixture was stirred for 4 days, diluted with dichloromethane, washed with 10% aqueous citric acid, dried (Na$_2$SO$_4$) and concentrated. The residue was purified by preparative TLC on silica gel (dichloromethane:methanol) to give the title compound (25 mg).

$\delta_H$ (400 MHz, CDCl$_3$): 7.52 (2H, m), 7.35–7.25 (3H, m), 6.95 (1H, dd, J 2.0 Hz, 8.9 Hz), 6.78 (1H, d, J 2.6 Hz), 6.67 (1H, d, J 8.9 Hz), 3.83 (1H, t, J 7.4 Hz), 3.77 (1H, br s), 3.71 (2H, m), 3.65 (3H, s), 3.70–3.50 (6H, m), 3.14 (1H, dd, J 5.1 Hz, 8.6 Hz), 2.75 (1H, br), 2.49 (1H, dd, J 8.6 Hz, 13.3 Hz), 2.43 (1H, dd, J 5.1 Hz, 13.3 Hz), 2.36 (1H, dd, J 7.8 Hz, 12.5 Hz), 2.19 (1H, ddt, J 2.7 Hz, 5.5 Hz, 12.9 Hz), 1.94 (1H, tt, J 7.0 Hz, 14.5 Hz), 1.85 (1H, dd, J 5.1 Hz, 14.1 Hz), 1.74 (1H, td, J 5.5 Hz, 12.9 Hz), 1.58 (2H, m), 1.43 (1H, dd, J 11.8 Hz, 12.1 Hz).

The hydrochloride salt of the title compound was prepared by treatment with ethereal HCl and recrystallisation from dichloromethane:tert-butyl methyl ether.

HCl salt: $\delta_H$ (360 MHz, MeOH-$d_4$): 7.52 (5H, m), 7.05 (1H, dd, J 1.9 Hz, 8.9 Hz), 6.87 (1H, d, J 9.0 Hz), 4.36 (1H, br s), 3.93 (1H, t, J 7.6 Hz), 3.80–3.50 (10H, m), 3.69 (3H, s), 3.14 (1H, dd, J 10.1 Hz, 14.1 Hz), 2.45 (.H, dd, J 5.0 Hz, 14.2 Hz), 2.40 (1H, dd, J 7.6 Hz, 13.2 Hz), 2.30 (1H, m), 2.14 (1H, dt, J 4.5 Hz, 13.7 Hz), 1.97 (1H, dd, J 4.7 Hz, 14.5 Hz), 1.97–1.81 (2H, m), 1.72 (1H, t, J 12.9 Hz), 1.19 (2H, s). MS (ES$^+$) 547 (M+H)$^+$.

EXAMPLE 21

(1R*,S2R*,4'S*,5R*)-2',3',4',5'-Tetrahydro-4'-(2-methoxy-5-trifluoromethoxyphenyl)-6-(3-methoxypropylaminocarbonyl)-8-phenylspiro[8-azabicyclo[3.2.1]octane-2,2'-furan]; and

EXAMPLE 22

(1R*,S2R*,4'S*,5R*)-2',3',4',5'-Tetrahydro-5-trifluoromethoxyphenyl)-6-(3-methoxypropylaminocarbonyl)-8-methyl-1-phenylspiro[8-azabicyclo[3.2.11]octane-2,2'-furan]

A portion of the solution from Step (a) of Example 20 (2 ml) was treated with 3-methoxypropylamine (0.15 ml, 1.94 mmol), triethyl amine (0.2 ml, 2.7mmol), 1-(3-dimethylaminopropyl)-3-ethylcarbodiimide hydrochloride (300 mg, 1.56 mmol), and 4-N,N-dimethylaminopyridine (20 mg, 0.16 mmol). The mixture was stirred for 4 days, diluted with dichloromethane, washed with 10% aqueous citric acid, dried ($Na_2SO_4$) and concentrated. The residue was purified by preparative TLC on silica gel (dichloromethane:methanol) to give (1R*,2R*,4S*,5R*)-2',3',4',5'-tetrahydro-6-(3-methoxypropylaminocarbonyl)-4'-(2-methoxy-5-trifluoromethoxyphenyl)-1-phenylspiro[8-azabicyclo[3.2.1]octane-2,2'-furan] (21 mg) and (1R*,2R*,4'S*,5R*)-2',3',4',5'-tetrahydro-6-(3-methoxypropylaminocarbonyl)-4'-(2-methoxy-5-trifluoromethoxyphenyl)-8-methyl-1-phenylspiro[8-azabicyclo[3.2.1]octane-2,2'-furan] (21 mg), Example 21: $\delta_H$ (360 MHz, $CDCl_3$): 7.40–7.25 (5H, m), 6.96 (1H, dd, J 2.6 Hz, 8.8 Hz), 6.75 (1H, d, J 2.7 Hz), 6.67 (1H, d, J 9.0 Hz), 3.79 (1H, t, J 7.7 Hz), 3.65 (3H, s), 3.64 (1H, t, J 2.3 Hz), 3.55 (1H, dd, J 7.7 Hz, 10.5 Hz), 3.30–3.12 (4H, m), 3.08 (3H, s), 2.77 (1H, dd, J 3.9 Hz, 9.5 Hz), 2.71 (1H, br), 2.54 (1H, dd, J 9.1 Hz, 13.3 Hz), 2.29 (1H, dd, J 7.7 Hz, 12.3 Hz), 2.25 (1H, dd, J 3.9 Hz, 13.3 Hz), 1.98 (1H, m), 1.88 (1H, m), 1.82–1.72 (2H, m), 1.68–1.55 (3H, m), 1.43 (1H, t, J 12.3 Hz).

Example 22: $\delta_H$ (360 MHz, $CDCl_3$): 7.59 (2H, dm, J 6.8 Hz), 7.40–7.30 (3H, m), 6.95 (1H, dd, J 2.0 Hz, 9.0 Hz), 6.73 (1H, d, J 2.7 Hz), 6.66 (1H, d, J 8.9 Hz), 3.96 (1H, t, J 7.7 Hz), 3.89 (1H, br s), 3.64 (3H, s), 3.59 (1H, dd, J 8.1 Hz, 10.9 Hz), 3.48 (3H, m), 3.39 (2H, m), 3.33 (3H, s), 3.11 (1H, dd, J 5.3 Hz, 13.7 Hz), 2.95 (1H, dd, J 5.6 Hz, 8.7 Hz), 2.38 (1H, br t, J 11.2 Hz), 2.27 (1H, dd, J 9.8 Hz, 13.7 Hz), 2.23 (3H, s), 2.13 (1H, dd, J 8.1 Hz, 12.6 Hz), 1.90 (1H, dd, J 4.6 Hz, 13.0 Hz), 1.85–1.67 (5H, m), 1.44 (1H, t, J 12.3 Hz). MS ($ES^+$) 550 $(M+H)^+$.

The hydrochloride salts of Example 21 and Example 22 were prepared by treatment with ethereal HCl.

HCl salt of Example 21: $\delta_H$ (360 MHz, MeOH-$d_4$): 7.52 (5H, m), 7.05 (1H, dd, J 1.6 Hz, 8.7 Hz), 6.86 (1H, d, J 8.9 Hz), 6.85 (1H, d, J 2.8 Hz), 4.20 (1H, s), 3.93 (1H, t, J 7.6 Hz), 3.68 (1H, m), 3.68 (3H, s), 3.42 (2H, t, J 6.1 Hz), 3.40–3.15 (6H, m), 2.95 (1H, dd, J 7.7 Hz, 9.8 Hz), 2.64 (1H, dd, J 4.6 Hz, 14.2 Hz), 2.40 (1H, dd, J 7.6 Hz, 13.2 Hz), 2.30 (1H, m), 2.10–1.80 (4H, m), 1.70–1.55 (3H, m), 1.17 (2H, s).

HCl salt of Example 22: $\delta_H$ (360 MHz, MeOH-$d_4$): 7.65–7.45 (5H, m), 7.04 (1H, ddd, J 1.1 Hz, 2.6 Hz, 8.8 Hz), 6.86 (1H, d, J 9.1 Hz), 6.83 (1H, d, J 2.9 Hz), 4.30 (1H, br s), 4.04 (1H, dd, J6.7 Hz, 8.5 Hz), 3.74 (1H, dd, J 8.2 Hz, 10.8 Hz), 3.67 (3H, s), 3.44 (2H, t, J 6.1 Hz),), 3.67 (1H, dd, J 5.5 Hz, 9.9 Hz), 3.40–3.15 (5H, m), 3.15 (1H, dd, J 5.8 Hz, 14.6 Hz), 2.86 (1H, dd, J 10.2 Hz, 14.6 Hz), 2.65 (3H, s), 2.43 (1H, m), 2.22 (1H, dd, J 7.0 Hz, 11.7 Hz), 2.17–2.01 (3H, m), 1.86–1.70 (4H, m). MS ($ES^+$) 564 $(M+H)^+$.

What is claimed is:
1. A compound of the formula (I):

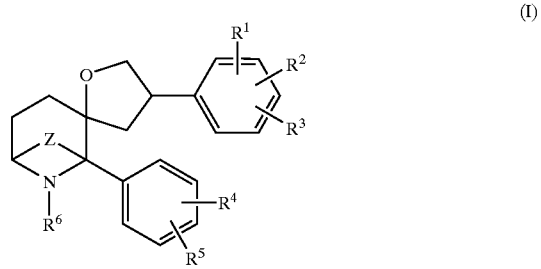

wherein

Z is —$CR^9R^{10}CH_2$— or —$CH_2CR^9R^{10}$—;

$R^1$ represents hydrogen, hydroxy, $C_{1-6}$alkyl, $C_{2-4}$alkenyl, $C_{3-7}$cycloalkyl, $C_{3-7}$cycloalkyl$C_{1-4}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$, $OSO_2R^a$, $NR^aCOR^{12}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen, sulphur, NH or $NR^c$, which ring is optionally substituted by one, two or three groups selected from hydroxy, $C_{1-4}$alkyl, $C_{1-3}$alkoxy$C_{1-3}$alkyl, fluoro$C_{1-4}$alkyl, phenyl, =O or =S, where $R^c$ is $C_{1-4}$alkyl, hydroxy$C_{1-4}$alkyl, $C_{1-4}$alkoxy$C_{1-4}$alkyl, fluoro$C_{1-4}$alkyl, phenyl or benzyl;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{12}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, C(S)NR$^a$R$^b$, CONR$^a$C$_{1-6}$alkylR$^{14}$, CONR$^{11}$C$_{2-6}$alkenyl, CONR$^{11}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from C$_{1-6}$alkyl, C$_{1-6}$alkoxy, halogen and trifluoromethyl);

or R$^6$ represents a group of the formula —CH$_2$C≡CCH$_2$NR$^7$R$^8$ where R$^7$ and R$^8$ are as defined below;

or R$^6$ represents C$_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —Y—NR$^7$R$^8$ where Y is C$_{1-6}$alkylene or C$_{3-6}$cycloalkyl;

R$^7$ represents hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^8$ represents hydrogen or C$_{1-4}$alkyl, C$_{1-4}$alkoxy, C$_{3-7}$cycloalkyl, C$_{3-7}$cycloalkylC$_{1-4}$alkyl, or C$_{2-4}$alkyl substituted by a group selected from C$_{1-4}$alkoxy, hydroxyl, CO$_2$R$^a$, NR$^a$R$^b$, aryl, aryloxy, heteroaryl or a 4, 5 or 6 membered heteroaliphatic ring containing one or two heteroatoms selected from N, O and S;

or R$^7$, R$^8$ and the nitrogen atom to which they are attached form a heteroaliphatic ring of 4 to 7 ring atoms, optionally substituted by one or two groups selected from hydroxy, phenyl, benzyl or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)2 or a second nitrogen atom which will be part of a NH or NR$^c$ moiety where R$^c$ is as previously defined;

or R$^7$, R$^8$ and the nitrogen atom to which they are attached form a non-aromatic azabicyclic ring system of 6 to 12 ring atoms;

or Y, R$^7$ and the nitrogen atom to which they are attached form a heteroaliphatic ring to 4 to 7 ring atoms which may optionally contain an oxygen ring atom;

R$^9$ represents hydrogen, hydroxy, oxo, C$_{1-6}$alkyl, C$_{2-6}$alkenyl, C$_{2-6}$alkalkynyl, C$_{3-7}$cycloalkyl, C$_{3-7}$cycloalkylC$_{1-4}$alkyl, fluoroC$_{1-6}$alkyl, C$_{1-6}$alkoxy, fluoroC$_{1-6}$alkoxy, hydroxyC$_{1-6}$alkyl, C$_{1-6}$alkoxyC$_{1-4}$alkyl, C$_{1-6}$alkoxyC$_{1-4}$alkoxy, fluoroC$_{1-6}$alkoxyC$_{1-4}$alkyl, C$_{2-6}$alkenyloxy, C$_{2-6}$alkynyloxy, C$_{3-7}$cycloalkoxy, C$_{3-7}$cycloalkylC$_{1-4}$alkoxy, aryl, aryl(CH$_2$), aryloxy, aryl(CH$_2$)oxy, cyano, halogen, NR$^7$R$^8$, CH$_2$NR$^7$R$^8$, SR$^{12}$, SOR$^{12}$, SO$_2$R$^{12}$, OSO$_2$R$^{12}$, NR$^a$COR$^{12}$, CH(OH)R$^{12}$, COR$^{12}$, CO$_2$R$^{12}$, CONR$^7$R$^8$, CH$_2$OR$^{13}$, heteroaryl or heteroarylC$_{1-4}$alkyl, wherein R$^a$ is as previously defined;

R$^{10}$ represents hydrogen, halogen or hydroxy;

R$^{11}$ represents hydrogen or C$_{1-6}$alkyl;

R$^{12}$ represents hydrogen, C$_{1-6}$alkyl, C$_{1-6}$alkoxy, fluoroC$_{1-6}$alkyl or phenyl optionally substituted by one, two or three substituents selected from C$_{1-6}$alkyl, C$_{1-6}$alkoxy, halogen or trifluoromethyl;

R$^{13}$ represents C$_{1-4}$alkyl substituted by a group selected from hydroxy, COR$^a$, CO$_2$R$^a$, CONR$^a$R$^b$ and heteroaryl, where R$^a$ is as previously defined;

R$^{14}$ represents OR$^a$, CONR$^a$R$^b$ or heteroaryl;

or a pharmaceutically acceptable salt or N-oxide thereof.

2. A compound as claimed in claim 1 wherein R$^1$ is a C$_{1-6}$alkoxy, fluoroC$_{1-6}$alkoxy or C$_{3-7}$cycloalkoxy group, or R$^1$ together with the group R$^2$ forms a 5-membered saturated ring containing one oxygen atom, which ring is optionally substituted by a methyl group.

3. A compound as claimed in claim 1 wherein R$^2$ is a hydrogen, fluorine or chlorine atom.

4. A compound as claimed in claim 1 wherein R$^3$ is a hydrogen or halogen atom or a fluoroC$_{1-6}$alkoxy group or a 5-membered aromatic heterocyclic group as defined in claim 1.

5. A compound as claimed in claim 1 wherein R$^4$ is hydrogen or fluorine.

6. A compound as claimed in claim 1 wherein R$^5$ is hydrogen.

7. A compound as claimed in claim 1 wherein R$^6$ is hydrogen or C$_{1-6}$alkyl, or a C$_{1-6}$alkyl group substituted by a 5-membered heterocyclic ring containing 2 or 3 nitrogen atoms as defined in claim 1.

8. A compound as claimed in claim 1 wherein Z is —CR$^9$R$^{10}$CH$_2$—.

9. A compound as claimed in claim 1 wherein R$^9$ is hydrogen, hydroxy, oxo, C$_{1-6}$alkoxy, C$_{1-6}$alkoxyC$_{1-4}$alkyl, hydroxyC$_{1-4}$alkyl, cyano, NR$^7$R$^8$, CH$_2$NR$^7$R$^8$, SO$_2$R$^d$, CH(OH)R$^{12}$, COR$^{12}$, CO$_2$R$^{12}$, CONR$^7$R$^8$, phenyl, heteroaryl, heteroarylC$_{1-4}$alkyl or CH$_2$OR$^{13}$, where said phenyl is optionally substituted by one or two substituents selected from C$_{1-4}$alkyl, C$_{1-4}$alkoxy, halogen or trifluoromethyl.

10. A compound as claimed in claim 1 wherein R$^{10}$ is hydrogen, fluorine or hydroxy.

11. A compound of the formula (Ia):

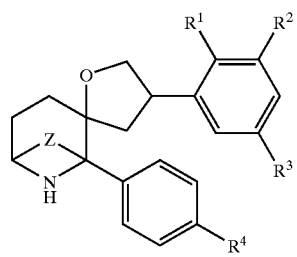

(Ia)

wherein R$^1$, R$^2$, R$^3$ and R$^4$ are as defined in claim 1 and Z is —CR$^9$R$^{10}$CH$_2$—;

or a pharmaceutically acceptable salt thereof.

12. A compound as claimed in claim 1 selected from:
(1R*,2R*,4'S*,5S*)-2',3',4',5'-tetrahydro-4'-(2-methoxy-5-trifluoromethoxyphenyl)-1-phenylspiro[8-azabicyclo[3.2.1]octane-2,2'-furan];
(1R*,2R*,4'S*,5S*,6R*)-2',3',4',5'-tetrahydro-4'-(2-methoxy-5-trifluoromethoxyphenyl)-1-phenyl-6-phenylsulphonylspiro[8-azabicyclo[3.2.1]octane-2,2'-furan];
(1R*,2R*,4'S*,5S*)-4'-(2-cyclopropyloxy-5-trifluoromethoxyphenyl)-2',3',4',5'-tetrahydro-1-phenylspiro[8-azabicyclo[3.2.1]octane-2,2'-furan];
(1R*,2R*,4'S*,5R*)-2',3',4',5'-tetrahydro-4'-(2-isopropoxy-5-trifluoromethoxyphenyl)-1-phenylspiro[8-azabicyclo[3.2.1]octane-2,2'-furan];
(1R*,2R*,4'S*,5R*)-2',3',4',5'-tetrahydro-4'-(2-(2',2'-difuoro)ethoxy-5-trifluoromethoxyphenyl)-1-phenylspiro[8-azabicyclo[3.2.1]octane-2,2'-furan];
(1R*,2R*,4'S*,5R*)-2',3',4',5'-tetrahydro-1-phenyl-4'-[2-(2,2,2-trifluoroethoxy)-5-trifluoromethoxyphenyl)spiro[8-azabicyclo[3.2.1]octane-2,2'-furan];
(1R*,2R*,4'S*,5R*)-4'-[2-(2-Fluoroethoxy)-5-trifluoromethoxyphenyl]-2',3',4',5'-tetrahydro-1-phenylspiro[8-azabicyclo[3.2.1]octane-2,2'-furan];

(1R*,2R*,4'S*,5S*)-2',3',4',5'-tetrahydro-4'-[(2RS)-2,3-dihydro-2-methyl-5-trifluoromethoxybenzofuran-7-yl]-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(morpholin-1-ylcarbonyl)-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(3-methoxypropylaminocarbonyl)-1-phenylspiro[8-azabicyclo[3.2.1]octane-2,2'-furan];

(1R*,2R*,4'S*,5R*)-2',3',4',5'-tetrahydro-4'-(2-methoxy-5-trifluoromethoxyphenyl)-6-(3-methoxypropylaminocarbonyl)-8-methyl-1-phenylspiro[8-azabicyclo[3.2.1]octane-2,2'-furan]; or a pharmaceutically acceptable salt thereof.

13. A compound as claimed in claim 1 wherein the stereochemistry of the 1- 2-, 4'- and 5-positions is as shown in formula (Ib):

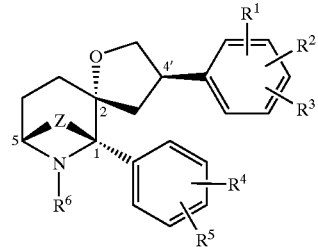

(Ib)

14. A pharmaceutical composition comprising a compound as claimed in claim 1, together with at least one pharmaceutically acceptable carrier or excipient.

15. A method for the treatment or prevention of physiological disorders associated with an excess of tachykinins, which method comprises administration to a patient in need thereof of a tachykinin reducing amount of a compound according to claim 1.

16. A method according to claim 15 for the treatment or prevention of pain or inflammation, migraine, emesis, postherpetic neuralgia, depression or anxiety.

* * * * *